(12) United States Patent
Guo et al.

(10) Patent No.: US 11,753,396 B2
(45) Date of Patent: Sep. 12, 2023

(54) HIERARCHICAL NANOPOROUS DIAMONDOID SUPERSTRUCTURE

(71) Applicants: Northwestern University, Evanston (SA); King Abdulaziz City for Science and Technology, Riyadh (SA)

(72) Inventors: Qing-Hui Guo, Evanston, IL (US); James Fraser Stoddart, Evanston, IL (US)

(73) Assignees: Northwestern University, Evanston, IL (US); King Abdulaziz City for Science and Technology, Riyadh (SA)

( * ) Notice: Subject to any disclaimer, the term of this patent is extended or adjusted under 35 U.S.C. 154(b) by 247 days.

(21) Appl. No.: 17/017,911

(22) Filed: Sep. 11, 2020

(65) Prior Publication Data

US 2021/0070736 A1 Mar. 11, 2021

Related U.S. Application Data

(60) Provisional application No. 62/898,904, filed on Sep. 11, 2019.

(51) Int. Cl.
*C07D 401/14* (2006.01)
*B82Y 30/00* (2011.01)

(52) U.S. Cl.
CPC .......... *C07D 401/14* (2013.01); *B82Y 30/00* (2013.01)

(58) Field of Classification Search
CPC .... B82Y 30/00; C07D 213/04; C07D 213/06; C07D 401/14
See application file for complete search history.

(56) References Cited

PUBLICATIONS

"Confirmation definition and meaning", https://www.dictionary.com/browse/confirmation, accessed Dec. 10, 2022 (Year: 2022).*
"Conformation", IUPAC Gold book, accessed Dec. 10, 2022, last revised 2014, attached as PDF (Year: 2014).*
Belcher. Organic and Biomolecular Chemistry, 2006, 4, 781-786 (Year: 2006).*
Dickson. New Journal of Chemistry, 2008, 32, 786-789 (Year: 2008).*
Jo. Polymer Preprints, 2011, 5(2), 387-388 (Year: 2011).*
Tanabe. Chemistry Letters, 2008, 37(12), 1208-1209 (Year: 2008).*
Tanabe. Journal of the American Chemical Society, 2012, 134, 5652-5661 (Year: 2012).*
Tanabe. Chemistry Letters, 2014, 43, 184-186 (Year: 2014).*
Aboutorabi, L., et al. "Metal-organic framework based on isonicotinate N-oxide for fast and highly efficient aqueous phase Cr (VI) adsorption." Inorganic Chemistry 55.11 (2016): 5507-5513.
Awci, C., et al. Self-assembly of polyhedral metal-organic framework particles into three-dimensional ordered superstructures. (2018). Nat. Chem. 10, 78-84.
Bale, J. B., et al. Accurate design of megadalton-scale two-component icosahedral protein complexes. (2016). Science 353, 389-394.
Banerjee, D., et al. "Zirconium-based metal-organic framework for removal of perrhenate from water." Inorganic Chemistry 55.17 (2016): 8241-8243.
Beaudoin, D., et al. Constructing monocrystalline covalent organic networks by polymerization. (2013). Nat. Chem. 5, 830-834.
Cao, L., et al. Diamondoid supramolecular coordination frameworks from discrete adamantanoid platinum(II) cages. (2018). J. Am. Chem. Soc. 140, 7005-7011.
Carrington, E. J., et al. Solvent-switchable continuous-breathing behaviour in a diamondoid metal-organic framework and its influence on CO2 versus CH4 selectivity. (2017). Nat. Chem. 9, 882-889.
Desai, A. V., et al. "A Water-Stable Cationic Metal-Organic Framework as a Dual Adsorbent of Oxoanion Pollutants." Angewandte Chemie (International ed. in English) 55.27 (2016): 7811-7815.
Ding, B, et al. "A unique multi-functional cationic luminescent metal-organic nanotube for highly sensitive detection of dichromate and selective high capacity adsorption of Congo red." RSC advances 6.40 (2016): 33888-33900.
Drout, R. J., et al. "Efficient capture of perrhenate and pertechnetate by a mesoporous Zr metal-organic framework and examination of anion binding motifs." Chemistry of Materials 30.4 (2018): 1277-1284.
El-Mehalmey, W. A., et al. "Metal-organic framework@ silica as a stationary phase sorbent for rapid and cost-effective removal of hexavalent chromium." Journal of Materials Chemistry A 6.6 (2018): 2742-2751.
Ermer, O. Five-fold diamond structure of adamantane-1,3,5,7-tetracarboxylic acid. (1988). J. Am. Chem. Soc. 110, 3747-3754.
Evans, O. R., et al. Crystal engineering of acentric diamondoid metal-organic coordination networks. (1999). Angew. Chem. Int. Ed. 38, 536-538.
Fei, H., et al. "Reversible anion exchange and catalytic properties of two cationic metal-organic frameworks based on Cu (I) and Ag (I)." Journal of the American Chemical Society 132.20 (2010): 7202-7209.
Fiedler, D., et al. Selective molecular recognition, C—H bond activation, and catalysis in nanoscale reaction vessels. (2005). Acc. Chem. Res. 38, 349-358.
Fu, H-R, et al. "Water-stable metal-organic frameworks for fast and high dichromate trapping via single-crystal-to-single-crystal ion exchange." Chemistry of Materials 27.1 (2015): 205-210.
Fujita, D., et al. Self-assembly of tetravalent Goldberg polyhedra from 144 small components. (2016). Nature 540, 563-566.

(Continued)

*Primary Examiner* — Noble E Jarrell
(74) *Attorney, Agent, or Firm* — QUARLES & BRADY LLP

(57) ABSTRACT

Disclosed herein are compositions, supramolecular assemblies, crystalline compositions, and methods of making and using the same. The composition comprises an organic ion and a counterion, wherein the organic ion comprises a molecular hub and arms extending therefrom and wherein the organic ion is capable of adopting a tripodal conformation.

19 Claims, 21 Drawing Sheets

(56) References Cited

PUBLICATIONS

Han, X., et al. Chiral 3d covalent organic frameworks for high performance liquid chromatographic enantioseparation. (2018). J. Am. Chem. Soc. 140, 892-895.

He Y-C et al., Luminescent anionic metal-organic framework with potential nitrobenzene sensing. Cryst. Growth Des. 14, 3174-3178 (2014).

He, T, et al. "Zr (IV)-based metal-organic framework with T-shaped ligand: unique structure, high stability, selective detection, and rapid adsorption of Cr2O72-in water." ACS applied materials & interfaces 10.19 (2018): 16650-16659.

He, Y., et al. A microporous hydrogen-bonded organic framework for highly selective C2H2/C2H4 separation at ambient temperature. (2011). J. Am. Chem. Soc. 133, 14570-14573.

Heinz, T., et al. Pairwise selection of guests in a cylindrical molecular capsule of nanometre dimensions. (1998). Nature 394, 764-766.

Hsia, Y., et al R. Design of a hyperstable 60-subunit protein icosahedron. (2016). Nature 535, 136-139.

Jones, J. T., et al. Modular and predictable assembly of porous organic molecular crystals. (2011). Nature 474, 367-371.

Kaphan, D. M., et al. A supramolecular microenvironment strategy fortransition metal catalysis. (2015). Science 350, 1235-1238.

Li, C-P, et al. "Highly efficient Cr 2 O 7 2-removal of a 3D metal-organic framework fabricated by tandem single-crystal to single-crystal transformations from a 1D coordination array." Chemical Communications 53.66 (2017): 9206-9209.

Li, X, et al. "A cationic metal-organic framework consisting of nanoscale cages: capture, separation, and luminescent probing of Cr2O72-through a single-crystal to single-crystal process." Angewandte Chemie International Edition 52.51 (2013): 13769-13773.

Li, Z., et al. Three-dimensional ionic covalent organic frameworks for rapid, reversible, and selective ion exchange. (2017). J. Am. Chem. Soc. 139, 17771-17774.

Lin, R. B. et al. Multifunctional porous hydrogen-bonded organic framework materials. (2019). Chem. Soc. Rev. 48, 1362-1389.

Lindeman, S. V., et al. The charge-transfer motif in crystal engineering. Self-assembly of acentric (diamondoid) networks from halide salts and carbon tetrabromide as electron-donor/acceptor synthons. (2003). J. Am. Chem. Soc. 125, 11597-11606.

Liu, Y. Z., et al. Supramolecular Archimedean cages assembled with 72 hydrogen bonds. (2011). Science 333, 436-440.

Lv, X-X, et al. "An unusual porous cationic metal-organic framework based on a tetranuclear hydroxyl-copper (II) cluster for fast and highly efficient dichromate trapping through a single-crystal to single-crystal process." Chemical Communications 53.11 (2017): 1860-1863.

Ma, T. Q., et al. Single-crystal x-ray diffraction structures of covalent organic frameworks. (2018). Science 361, 48-52.

MacGillivray, L. R. et al. A chiral spherical molecular assembly held together by 60 hydrogen bonds. (1997). Nature 389, 469-472.

MacNicol, D. D., et al. Crystal and molecular structure of a 'hexa-host' inclusion compound. (1977). Nature 266, 611-612.

Mal, P., et al. White phosphorus is air-stable within a self-assembled tetrahedral capsule. (2009). Science 324, 1697-1699.

Mastalerz, M. et al. Rational construction of an extrinsic porous molecular crystal with an extraordinary high specific surface area. (2012). Angew. Chem. Int. Ed. 51, 5252-5255.

Olenyuk, B., et al. Self-assembly of nanoscale cuboctahedra by coordination chemistry. (1999). Nature 398, 796-799.

Pasquale, S., et al. Giant regular polyhedra from calixarene carboxylates and uranyl. (2012). Nat. Commun. 3, 785-791.

Pluth, M. D., et al. Acid catalysis in basic solution: A supramolecular host promotes orthoformate hydrolysis. (2007). Science 316, 85-88.

Rapti, S, et al. "All in one porous material: exceptional sorption and selective sensing of hexavalent chromium by using a Zr 4+ MOF." Journal of Materials Chemistry A 5.28 (2017): 14707-14719.

Rapti, S, et al. "Selective capture of hexavalent chromium from an anion-exchange column of metal organic resin-alginic acid composite." Chemical science 7.3 (2016): 2427-2436.

Rebek, J., Jr. Simultaneous encapsulation: molecules held at close range. (2005). Angew. Chem. Int. Ed. 44, 2068-2078.

Rizzuto, F. J. et al. Stereochemical plasticity modulates cooperative binding in a Co(II)12L6 cuboctahedron. (2017). Nat. Chem. 9, 903-908.

Ryder, MR et al. Understanding and controlling the dielectric response of metal-organic frameworks. ChemPlusChem 83, 308-316 (2018).

Schwertfeger, H., et al. Diamonds are a chemist's best friend: diamondoid chemistry beyond adamantane. (2008). Angew. Chem. Int. Ed. 47, 1022-1036.

Sheng, D., et al. "Efficient and selective uptake of TcO4-by a cationic metal-organic framework material with open Ag+ sites." Environmental science & technology 51.6 (2017): 3471-3479.

Simard, M., et al. Use of hydrogen bonds to control molecular aggregation. Self-assembly of three-dimensional networks with large chambers. (1991). J. Am. Chem. Soc. 113, 4696-4698.

Tian, J., et al. Three-dimensional periodic supramolecular organic framework ion sponge in water and microcrystals. (2014). Nat. Commun. 5, 5574-5584.

Yamagishi, H., et al. Self-assembly of lattices with high structural complexity from a geometrically simple molecule. (2018). Science 361, 1242-1246.

Zaworotko, M. J. Crystal engineering of diamondoid networks. (1994). Chem. Soc. Rev. 23, 283-288.

Zhang, C, et al. "A Zwitterionic Ligand-Based Cationic Metal-Organic Framework for Rapidly Selective Dye Capture and Highly Efficient Cr2O72-Removal." Chemistry—A European Journal 24.11 (2018): 2718-2724.

Zhang, Q, et al. "A porous Zr-cluster-based cationic metal-organic framework for highly efficient Cr 2 O 7 2-removal from water." Chemical Communications 51.79 (2015): 14732-14734.

Zhu, L, et al. "Exceptional perrhenate/pertechnetate uptake and subsequent immobilization by a low-dimensional cationic coordination polymer: overcoming the hofmeister bias selectivity." Environmental Science & Technology Letters 4.7 (2017): 316-322.

Zhu, L, et al. "Identifying the recognition site for selective trapping of 99TcO4-in a hydrolytically stable and radiation resistant cationic metal-organic framework." Journal of the American Chemical Society 139.42 (2017): 14873-14876.

* cited by examiner

| Y | X |
|---|---|
| N | Cl |
| N | Br |
| N | PF₆ |
| N | AsF₆ |
| CH | PF₆ |

1, Y = N; 2, Y = CH
1·6X and 2·6X
Ionic Molecules $D_{3d}$ Conformation

Three Types of $PF_6^-$

[C–H···F] Interactions

Tetrahedral Subunit

Edge

Face

Vertex-Sharing Tetrahedra

Supramolecular Diamond Unit    Nanopore

Nanoporous Supramolecular Diamond

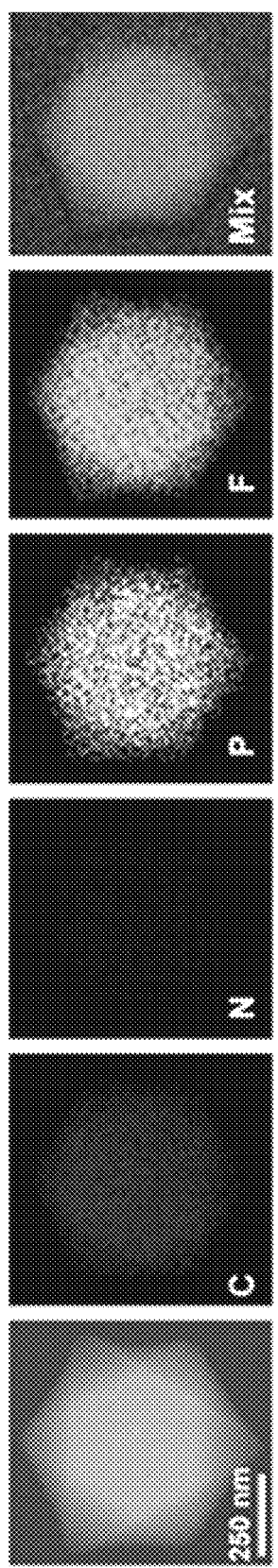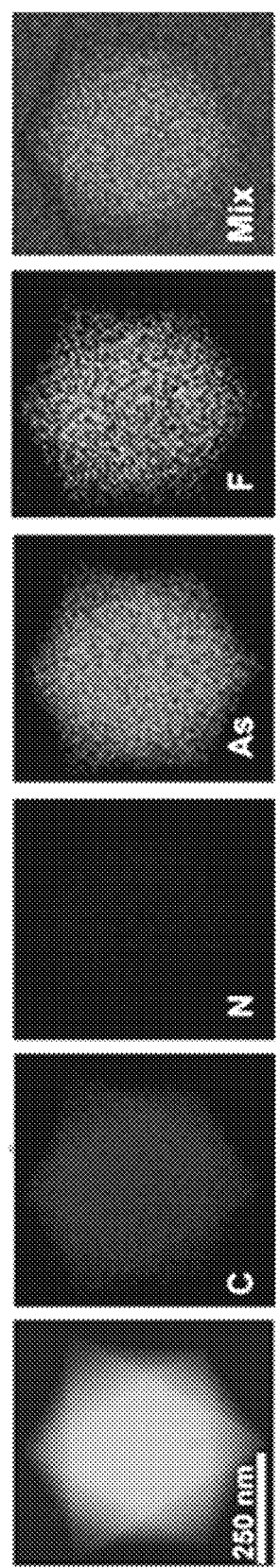

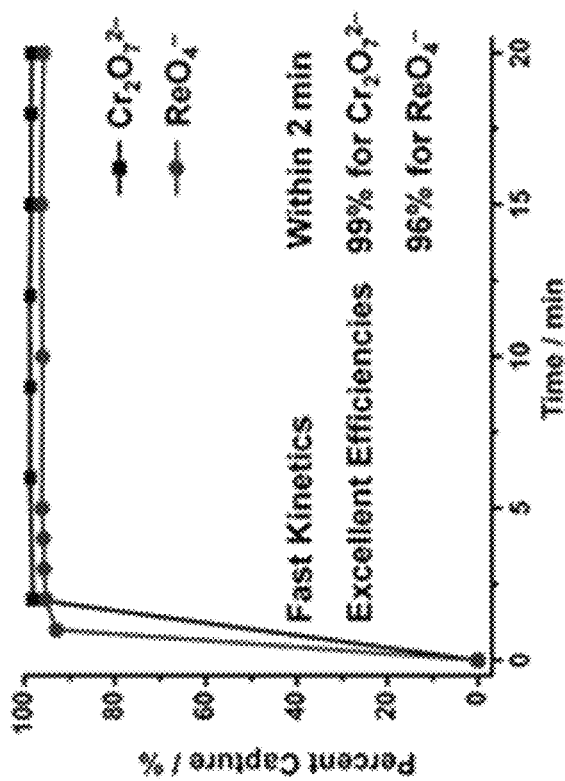
Fig. 4B
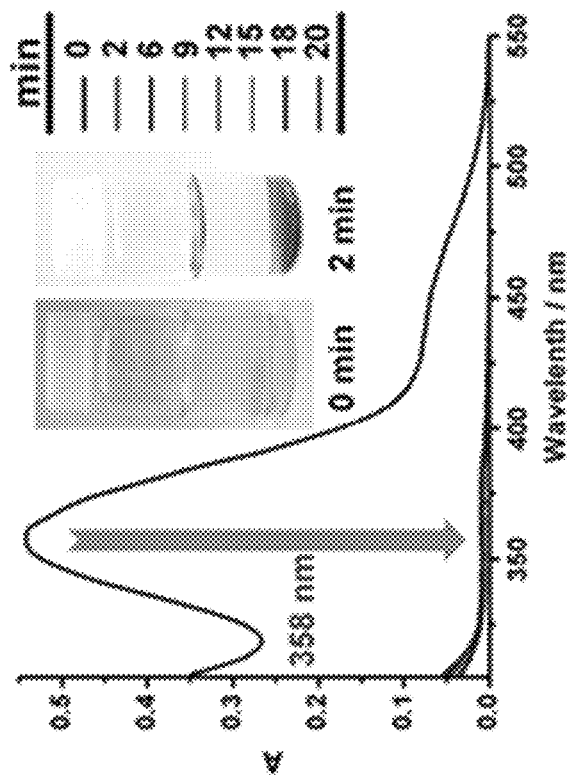
Fig. 4C
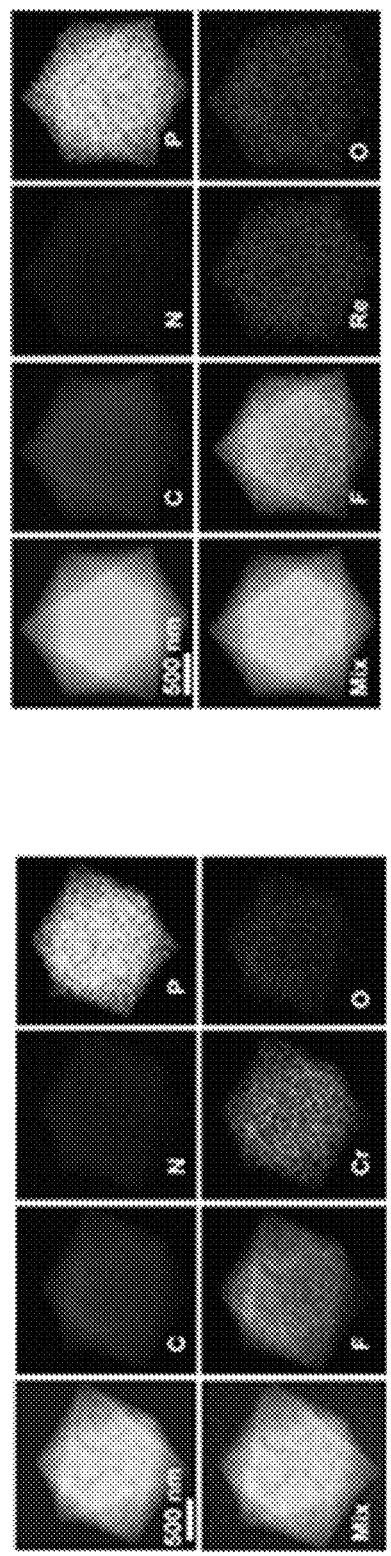
Fig. 4D
Fig. 4E

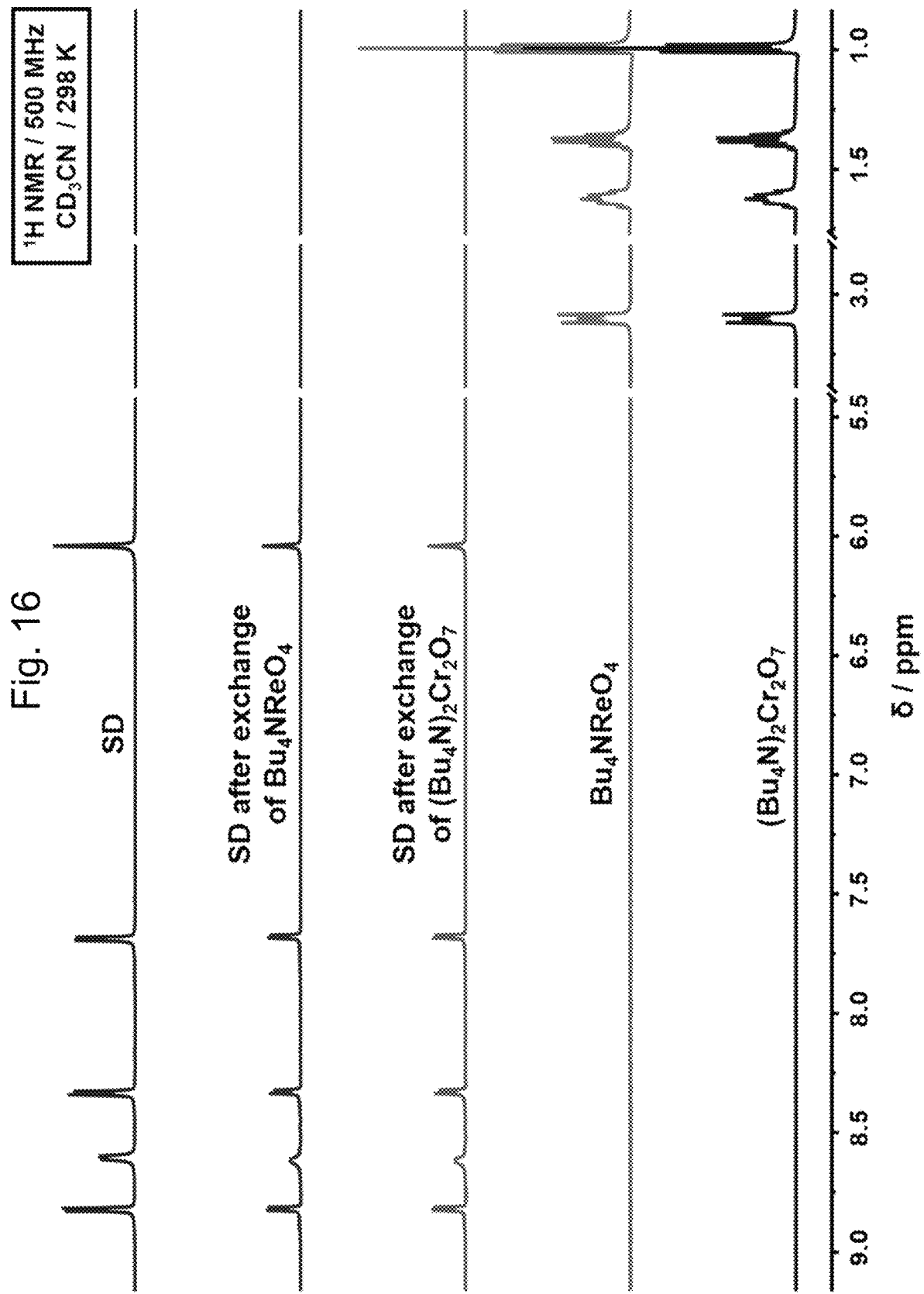

HIERARCHICAL NANOPOROUS DIAMONDOID SUPERSTRUCTURE

CROSS-REFERENCE TO RELATED APPLICATIONS

This application claims benefit of priority to United States Provisional Application 62/898,904, filed Sep. 11, 2019, the contents of which are incorporated herein in its entirety.

BACKGROUND

Multivalent self-assembly of small components into large, complex, and functional superstructures through cooperative interactions is a ubiquitous phenomenon in Nature[1,2]. In order to mimic the various functions and unravel the mechanisms involved in the precise self-assembly processes, investigators have devoted substantial efforts to the design and synthesis of assemblies with well-defined superstructures, including supra-molecular cages and capsules[3,4], organic and metal-coordinated polyhedra[5-9] and nanoshells[10], as well as protein polyhedra[11,12]. These aesthetically beautiful supramolecular assemblies, with tailorable interior cavities, have applications as diverse as in molecular recognition and separation[13,14], drug delivery[15], stabilization of reactive molecules[16], and catalysis[17,18], to name but a few general categories. The efficient construction of periodic supramolecular assemblies with hierarchical superstructures from simple and identical building blocks[19] purely by relying on noncovalent bonding interactions, reminiscent of those in Nature[20], however, is both elusive and highly desirable.

BRIEF SUMMARY OF THE INVENTION

Disclosed herein are compositions, supramolecular assemblies, crystalline compositions, and methods of making and using the same. The composition comprises an organic ion and a counterion. The organic ion may comprise a molecular hub and arms extending therefrom and is capable of adopting a tripodal conformation. The organic ion may be comprised of a benzene ring molecular hub and/or bipyridinium arms extending therefrom. Suitably the organic ion is hexacationic. The counter ion may be a hexafluoride, such as $PF_6^-$ or $AsF_6^-$. The organic ion may be hexakis[(4,4'-bipyridin-1-ium)methylene]benzene.

Another aspect of the invention is supramolecular assemblies comprising any of the compositions described herein wherein four organic ions may form a truncated tetrahedral subunit. The counterion may be positioned within a cavity formed by the organic ion in the tripodal conformation. Suitably the organic ion has $D_{3d}$ symmetry. In some embodiments, the neighboring truncated tetrahedral subunits share the molecular hub as a vertex. In some embodiments, ten truncated tetrahedral subunits form a diamondoid unit. Suitably, the diamondoid unit forms a pore.

Another aspect of the invention comprises crystalline compositions comprising any of the compositions or supramolecular assemblies described herein. The crystalline composition may be in the cubic, $Fd\bar{3}$ space group. The crystalline composition may be porous. In some embodiments, the crystalline composition has a solvent-accessible void of at least 50%. In some embodiments, the crystalline composition has a unit cell comprising 16 organic ions. The crystalline composition may further comprise a second counterion. Suitably, the second counteranion is an oxoanion.

Methods of preparing the compositions, supramolecular assemblies, and crystalline compositions are also provided for. The supramolecular assembly or crystalline composition may be prepared by precipitating a solution comprising any of the composition described herein. Suitably, the solution is precipitated by mixing the solution with an anti-solvent or by slow vapor diffusion of an anti-solvent. The method may further comprise exchanging at least a portion of the counterion with a second counterion.

Another aspect of the invention is methods for sequestering ionic contaminants. The method may comprise contacting any of the supramolecular assemblies or crystalline compositions described herein with the ionic contaminant. Suitably, the contacting steps exchanging at least a portion of the counterion within the supramolecular assembly or crystalline composition with the ionic contaminant. Suitably the ionic contaminant is an oxoanion.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 1A) Structural formulas of the molecular cations. (FIG. 1B) $D_{3d}$ Symmetric tripodal conformation of $1^{6+}$. (FIG. 1C) Three types of $PF_6^-$ counteranions, type-I, -II and -III. (FIG. 1D) The type-I $PF_6^-$ anions locating in the cavities maintain the tripodal conformation through multiple [C—H . . . F] interactions which are depicted as dashed lines. (FIG. 1E) Structure of noncovalent connecting truncated tetrahedral subunit with four type-I $PF_6^-$ anions inside the cavity. (FIG. 1F) The edge of the tetrahedral subunit. The [C—H . . . N] interactions are depicted as black dashed lines and the [π . . . π] interactions are depicted as cyan dashed lines. (FIG. 1G) The facet of the tetrahedral subunit with type-II $PF_6^-$ anion in the centroid. The [C—H . . . F] interactions are depicted as dashed lines. (FIG. 1H) Tetrahedral subunits connecting vertex-sharing of the benzene ring.

(FIG. 2A) Ten tetrahedral subunits assemble into one supramolecular diamond unit with a 1.8 nm interior pore, which is depicted as a ball. (FIG. 2B) The nanoporous framework of SD with hexagonal channels wherein type-III $PF_6^-$ anions are aligned inside. Although all the tetrahedral subunits are identical in symmetry, they are depicted with different shading in order to differentiate the connecting patterns in the superstructure.

FIGS. 3A-3E show SEM and (S)TEM characterization of size-controllable and crystalline supramolecular diamond with uniform morphology. (FIG. 3A) SEM images at lower magnification (right) and higher magnification (left) and (FIG. 3B) TEM images at lower magnification (right) and higher magnification (left) of uniform octahedral supramolecular diamond 1·6$PF_6^-$ prepared by solvent-induced precipitation. (FIG. 3C) Photographs and SEM images of octahedral SD 1•6PF$_6$ with controllable sizes of 660 µm, 45 µm, 3 µm, 750 nm, and 280 nm. STEM-EDS Maps show the homogeneity of the samples SD 1•6PF$_6$ (FIG. 3D) and 1•6AsF$_6$ (FIG. 3E) with all the component elements well-distributed within the crystals.

FIGS. 4A-4E show the mobilities of PF$_6^-$ anions and cationic nanoporosity in the single-crystal-to-single-crystal (SCSC) transformation of supramolecular diamond and the anion exchanges with dichromate and perrhenate. (FIG. 4A) SCSC transformation from fresh SD 1•6PF$_6$ to soaked SD 1a•6PF$_6$ in iPrOH. The fixed PF$_6^-$ anions inside the tetrahedra are highlighted in space-filling representations. The mobile PF$_6^-$ anions are shown as ball-stick representations. The organic skeletons are illustrated as stick representation. (FIG. 4B) The process of anion exchange with Cr$_2$O$_7^{2-}$ was monitored by UV/Vis spectroscopy. The inset shows discoloration of the supernatant solution after 2 min. (FIG. 4C) The exchange isotherms of Cr$_2$O$_7^{2-}$ and ReO$_4^-$ with fast kinetics and excellent efficiencies. STEM-EDS maps show SD sustaining the morphologies after anion exchanges with (FIG. 4D) Cr$_2$O$_7^{2-}$ and (FIG. 4E) ReO$_4^-$ along with the presence of corresponding metal elements and partial residue of phosphorus and fluorine element.

FIG. 13A shows the amount of the adsorbed Cr$_2$O$_7^{2-}$ (q) as a function of extraction time at various exposure concentrations. FIG. 13B shows the Type I, linear Langmuir plot for Cr$_2$O$_7^{2-}$ capture by SD 1•6PF$_6$.

FIG. 15A shows an exemplary process of capturing an oxoanion, such as dichromate, and the regeneration of SD. FIG. 15B shows PXRD of SD soaked in EtOH, iPrOH, and after anion extraction with ReO$_4^-$ and Cr$_2$O$_7^{2-}$.

FIG. 16 shows $^1$H NMR spectra of SD after anion extraction of ReO$_4^-$ and Cr$_2$O$_7^{2-}$.

FIG. 17A shows the concentrations of Cr$_2$O$_7^{2-}$ dianions and PF$_6^-$ anion in the solution of Cr$_2$O$_7^{2-}$ dianions during the anion exchange process. FIG. 17B shows the concentrations of ReO$_4^-$ anion and PF$_6^-$ anion in the solution of ReO$_4^-$ anion during the anion exchange process.

DETAILED DESCRIPTION OF THE INVENTION

Figure 1A:
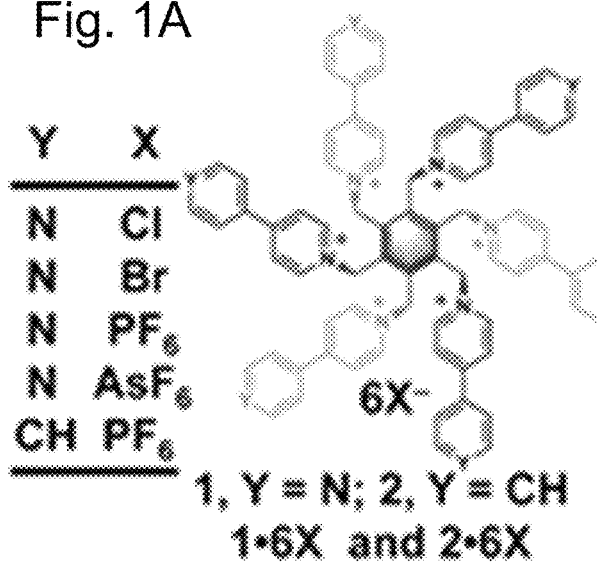
FIGS. 1A-1H show single-crystal (super)structures of 1·6$PF_6$ and the tetrahedral subunit at Level 1 (FIG. 1A-1D) and Level 2 (FIG. 1E-1D).

Disclosed herein are compositions, supramolecular assemblies, crystalline compositions, and methods of making and using the same. Here, we describe a highly ordered three-dimensional (3D) hierarchical supramolecular architecture constructed by the multiple-level self-assembly of topologically simple salts, such as hexakis[(4,4'-bipyridin-1-ium)methylene]benzene hexafluorophosphate 1•6PF$_6$ or hexakis[(4,4'-bipyridin-1-ium)methylene]benzene hexafluoroarsenate 1•6AsF$_6$.

The compositions, supramolecular assemblies, crystalline compositions comprise an organic ion capable of adopting a tripodal conformation and a counter ion. The counterion may be located within a cavity formed by the tripodal conformation and the interaction of the organic ion and the counterion provide stability for the supramolecular assemblies and crystalline compositions described herein.

The organic ion comprises a molecular hub and arms extending therefrom. The molecular hub may be a planar structure having three-fold or a multiple of three-fold symmetry. Each of the atoms of the molecular hub may be covalently bonded with an arm. In some embodiments, the molecular hub has six-fold symmetry, such as a benzene ring. Suitably, each of the six carbon atoms of a benzene ring may be covalently bond with an arm. Conformational flexibility of the arms around the molecular hub provide the organic ion the ability to adopt a tripodal conformation. As used herein, a "tripodal conformation" means a conformation where the organic ion has three arms extending in substantially the same direction out of normal to the planar characterizing the molecular hub. Suitably, when the molecular hub comprises six arms, the organic ion may adopt a double tripod conformation. As used herein, a "double tripodal conformation" means a conformation where the organic ion has three arms extending in substantially the same direction out of normal to the planar characterizing the molecular hub and another three arms extending in the opposite direction out of normal to the planar characterizing the molecular hub. The double tripod conformation may have D$_{3d}$ symmetry.

The arms of the organic ion are capable of interacting with each other through various noncovalent interactions. These noncovalent interactions include hydrogen bonding and [π . . . π] interactions. The arms may include an extended aromatic system that may provide rigidity to the arms. Suitably, the arms comprise one or more aromatic ring and the rings may be heteroaromatic rings comprising one of more non-carbon atoms such as nitrogen, oxygen, or sulfur. Suitably, the arms of the organic ion comprise bipyridinium arms, such as (4,4'-bipyridin-1-ium)methylene arms as described herein. When the organic ion comprises bipyridinium arms, each of the arms may carry a 1+ charge. When the organic ion comprises six bipyridinium arms, the organic ion may suitably be hexacationic. In some embodiments, the organic ion is hexakis[(4,4'-bipyridin-1-ium)methylene]benzene.

The compositions described here suitably include a counterion that allows for the formation of the supramolecular assembly and crystalline compositions described herein. Suitably the counterion is a hexafluoride, such as PF$_6^-$ or AsF$_6^-$.

Because of mobile counterions in the supramolecular assembly and crystalline compositions, the compositions described herein may suitably be used to sequester ionic contaminants via ion exchange. The ionic contaminant may be any undesirable ion, such as a radioactive ion, an environmental contaminant, or a hazardous material.

In some embodiments, the ionic contaminant is an oxoanion. "Oxoanions", which may also be referred to as "oxyanions", are polyatomic negatively charged ions containing oxygen with the generic formula $A_xO_y^{z-}$, where A represents a chemical element and O represents an oxygen atom. Metal or metaloid oxyanions are characterized by toxicity, non-biodegradability, and high solubility in water, which makes them extremely mobile harmful species which easily bioaccumulate in the environment and in the food chain. These species may be very dangerous even at low concentrations. Exemplary oxoanions may include elements A, such as Cr, Tc, Re, As, Se, Mo, W, B, and V. In some embodiments, the oxoanion comprises Cr(VI), Tc(IV), Re(IV), As(III), As(V), Se(IV), Se(VI), Mo(VI), and U(VI).

The superstructure of the compositions comprising the organic ion and the counterion, such as 1•6PF$_6$ and 1•6PF$_6$, exhibits a hierarchical framework[21], which is exactly the same as that of a natural diamond, with noncovalently connected tetrahedral subunits substituting for the carbon atoms in a diamond as building blocks. As a result, we use the name "supramolecular diamond" or "SD" to describe this highly periodic, structurally complex, noncovalently bonded, hierarchically diamondoid, and intrinsically cationic assembly. Our design relies on the preorganized conformation of the hexacationic organic ion, such as hexakis[(4,4'-bipyridin-1-ium)methylene]benzene $1^{6+}$, and the combination of multiple weak interactions—hydrogen bonding and [π . . . π] interactions—with both complementarity and synergy working in concert. The hierarchical architecture of the infrequent assembly was unambiguously elucidated by single-crystal X-ray diffraction (SCXRD). Using our strategy, octahedral crystals of SD can be prepared quantitatively in a rapid one-step procedure at room temperature by simply mixing two solutions. The resulting SD samples possess uniform morphologies, controllable sizes and high crystallinity, which are fully supported by scanning electron microscopy (SEM), (scanning) transmission electron microscopy ((S)TEM) imaging and powder X-ray diffraction (PXRD). Some counteranions in the SD are mobile and this results in a single-crystal-to-single-crystal (SCSC) transformation. The mobilities of counteranions and 3D intrinsically cationic nanoporosity are further demonstrated by the excellently efficient anion exchanges with hazardous metal oxoanions.

Figure 1B:
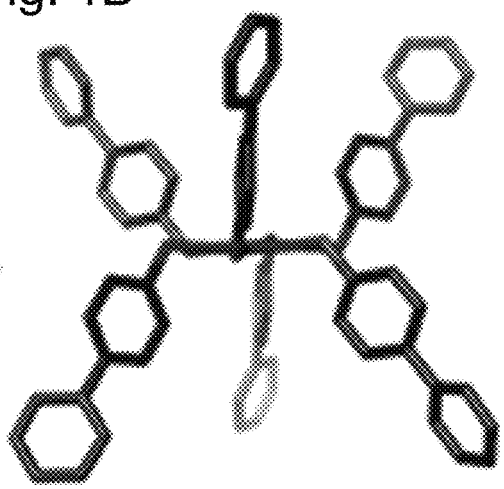
Figure 1C:
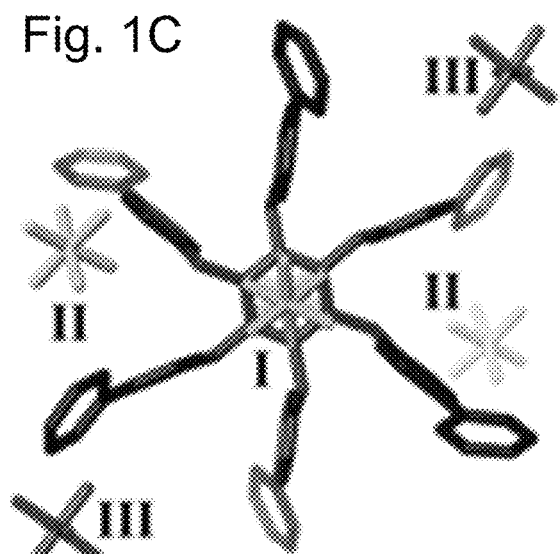
Figure 1D:
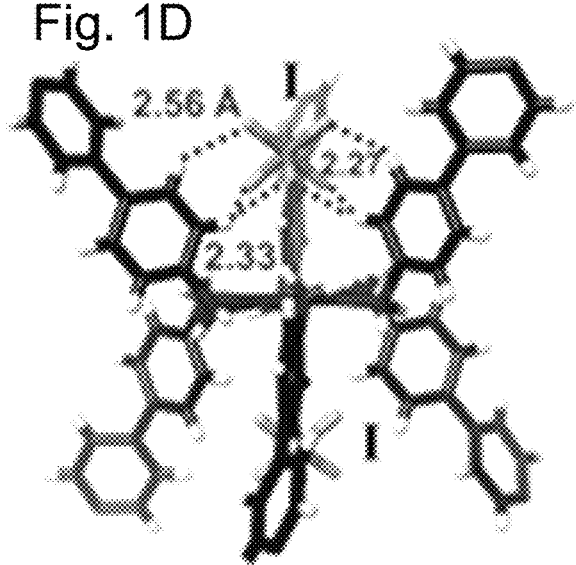

The unique 3D framework structure of diamond endows it with the distinctively well-known properties, such as high stability, extreme hardness, and thermal conductivity[21]. In order to obtain the intrinsic properties, scientists have attempted to design and construct diamondoid frameworks at the atomic level in well-controlled manners[22,23]. Ordered diamondoid frameworks, especially porous materials, such as diamondoid metal-organic frameworks (MOFs)[24,25], covalent organic frameworks (COFs)[26-29], and supramolecular porous frameworks[30-36], have long been investigated. It is a general principle that tetrahedral building blocks with Td or pseudo Td symmetry—e.g., sp$^3$-hybridized tetrahedral carbon atoms—are a prerequisite to forming complex diamondoid frameworks[22]. By employing the principles of supramolecular chemistry, we present an unprecedented strategy for constructing a hierarchical diamondoid framework from simple cationic species with $D_{3d}$ symmetry in a controllable one-step procedure at a mild condition. In our strategy, the building block $1^{6+}$ (FIG. 1A) with six positively charged arms connected to one central benzene ring is expected[37] to adopt a preorganized $D_{3d}$ conformation (FIG. 1B). The preorganized molecules, with the assistance of appropriate counteranions, unexpectedly self assemble into a hierarchical diamondoid architecture by multivalent assembly. In order to establish the main driving forces and get insight into the mechanism for the formation of SD, a series of similar compounds with different counterions or pendant arms (FIG. 1A) were also designed. Their single-crystal structures and electronic band gaps were analyzed. All the compounds were synthesized efficiently from commercially available starting materials by nucleophilic substitution (S$_N$2) reactions, followed by counterion exchanges, in excellent yields on a multi-gram scale (Schemes 1-5).

Hierarchical Diamondoid Architecture

Figure 1E:
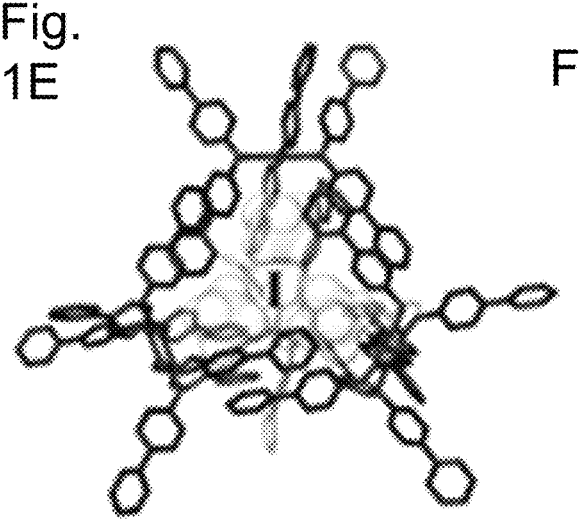
Figure 1F:
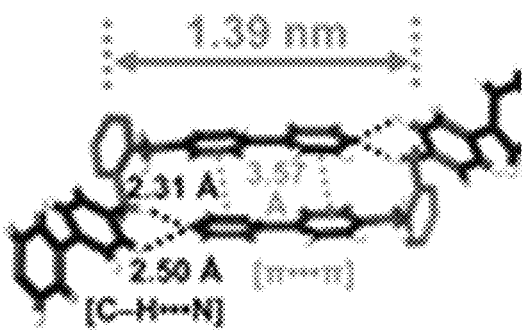
Figure 1G:
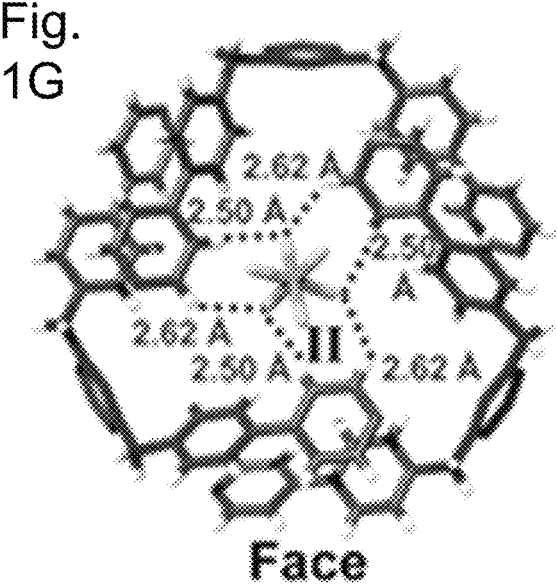
Figure 1H:
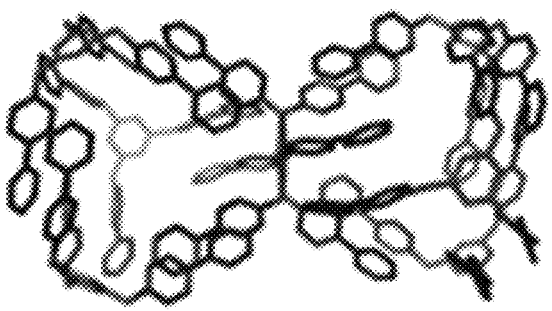
Figure 7:
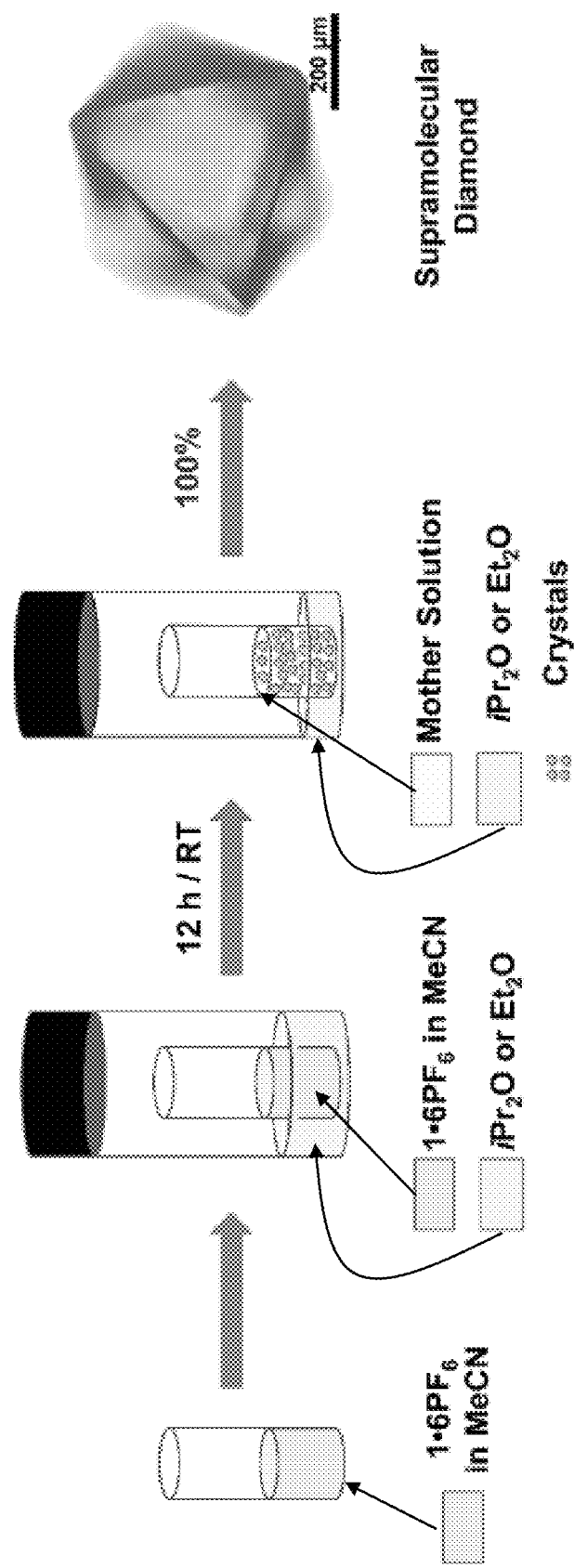
FIG. 7 shows a schematic view of the preparation of SD 1•6PF$_6$ with sizes ranging from 45 to 660 µm.

Golden yellow octahedral single crystals suitable for SCXRD were obtained by slow vapor diffusion of diisopropyl ether (iPr$_2$O) into a solution of 1•6PF$_6$ in acetonitrile (MeCN) (FIG. 7). These crystals with regular octahedral shapes have sizes as large as 660 μm—defined as the distance between two opposing vertices. SCXRD with a resolution of 0.85 Å reveals a hierarchical diamondoid superstructure with a cubic Fd$\bar{3}$ space group (a=39.3486 Å) and a unit cell volume of 60923.9(5) Å$^3$. The high crystallinity of the metal-free porous single crystals of 1•6PF$_6$ is quite unexpected 29 since the solvent-accessible voids account for 52% of the whole unit cell volume. The high quality of the crystallographic data enables the accurate identification of all the discrete components, 96 cationic organic fragments and 96 counteranions, within the unit cell. As a basic building block within the solid-state superstructure, the cationic fragment of $1^{6+}$ adopts (FIG. 1B) a tripodal conformation wherein three monobipyridinium arms are oriented up and the other three down, in an alternating manner, in order to minimize the Coulombic repulsive interactions between neighboring monobipyridinium cations. Because of their locations, the six PF$_6^-$ counteranions, surrounding the organic skeleton, can be grouped (FIG. 1C) into three sets: type-I, -II and -III, respectively. Two type-I PF$_6^-$ anions located in the two opposite cavities delineated by the benzene ring holding all three monobipyridinium arms on the same side together by means of multiple [C—H . . . F] interactions ($d_{[F \ldots H]}$=2.27, 2.33 and 2.56 Å, FIG. 1D) to organize $1^{6+}$ in a double-sided tripodal $D_{3d}$ conformation. The construction of this defined molecular conformation by the interplay of the conformational preference of $1^{6+}$ with the assistance of the counteranions represents the Level 1 assembly hierarchy (FIGS. 1A to 1D). These ionic molecules in Level 1 assemble to create the hierarchy of Level 2 (FIGS. 1E to 1H). Four 1•6PF$_6$ salt units assemble into a truncated tetrahedron with four type-I PF$_6^-$ counteranions located inside the cavity (FIG. 1E). Each vertex of the truncated tetrahedron is composed of one $1^{6+}$ hexacation. Each edge of the truncated tetrahedron, with a length of 1.39 nm—the distance between the centroids of two neighboring benzenes—consists (FIG. 1F) of two monobipyridinium arms from two adjacent $1^{6+}$ hexacations in an anti-parallel manner by means of synergistic directional [C—H . . . N] ($d_{[N \ldots H]}$=2.31 and 2.50 Å) and [π . . . π] interactions ($d_{[centroid \ldots centroid]}$=3.57 Å). The [C—H . . . N] interactions occur between the terminal nitrogen atoms of the monobipyridinium cations with both the H$_\alpha$ atoms from adjacent monobipyridinium arms and one of the CH$_2$ protons of the adjacent $1^{6+}$ hexacation. Each triangular facet of the truncated tetrahedra is composed (FIG. 1G) of three aforementioned edges from three adjacent $1^{6+}$ hexacations which encircle a type-II $PF_6^-$ counteranion at the center by means of six [C—H . . . F] interactions ($d_{[F \ldots H]}$=2.50 and 2.62 Å). In addition, three MeCN molecules are located at the corners of the triangular facet through multiple [C—H . . . N] interactions. Each triangular face of the truncated tetrahedral subunit consists of three edges from three adjacent molecules surrounding one $PF_6^-$ anion through multiple [C—H . . . F] interactions. Three MeCN molecules locate the corners of the triangular face through multiple [C—H . . . N] interactions. MeCN solvents are essential for building SD superstructures. DMF and $MeNO_2$ both failed to afford SD single crystals. The truncated tetrahedral subunits extend (FIG. 1H) together by sharing one benzene ring.

Figure 2A:
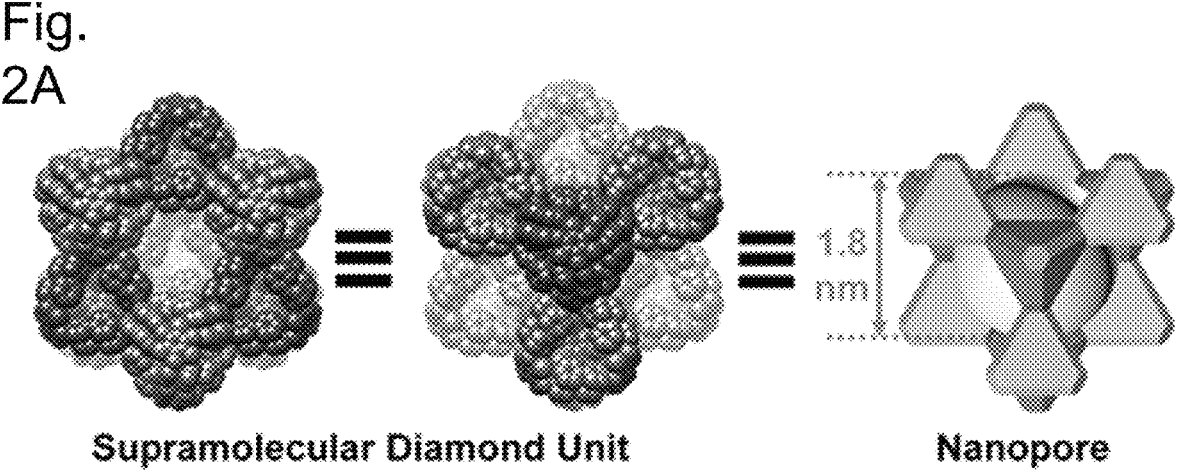
FIGS. 2A-2B show space-filling representations of single crystal superstructures of the supramolecular diamond unit and nanoporous supramolecular diamond at Level 3 (FIG. 2A) and Level 4 (FIG. 2B).
Figure 2B:
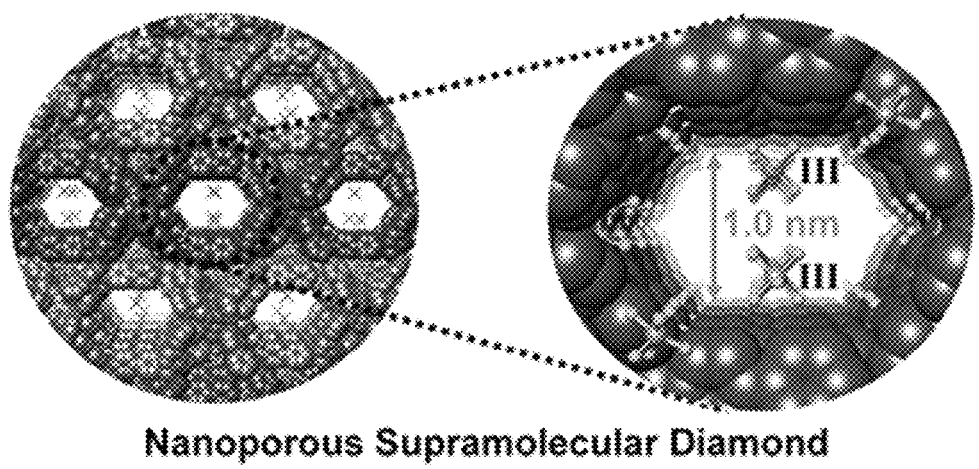
Figure 5:
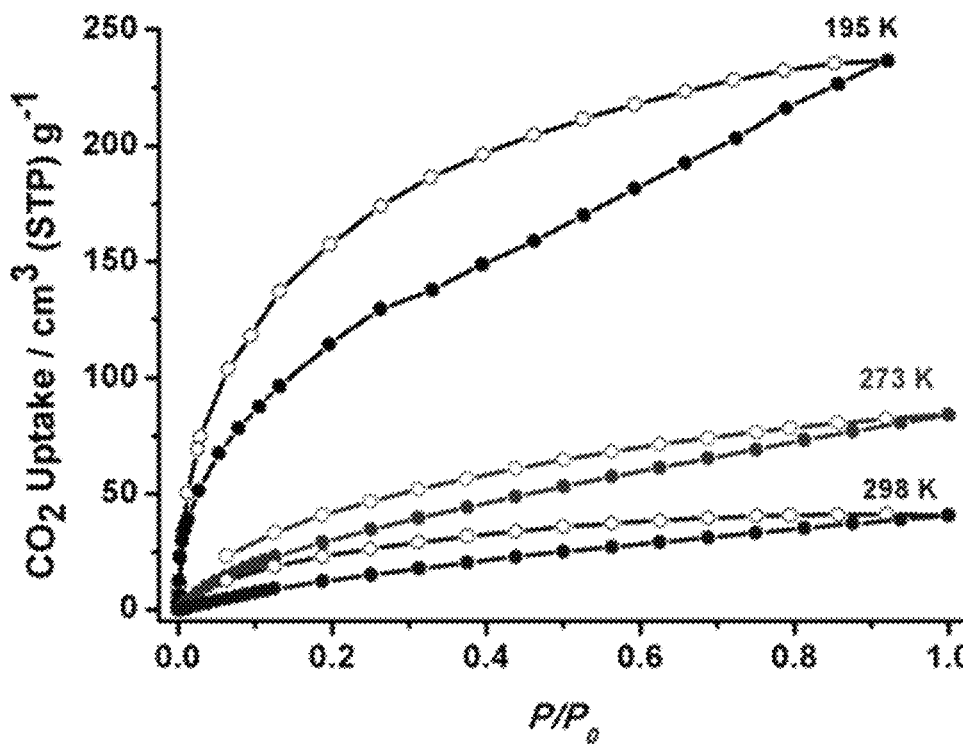
FIG. 5 shows CO$_2$ Adsorption (filled symbols) and desorption (open symbols) isotherms of SD 1•6PF$_6$ at 195, 273, and 298 K.
Figure 6:
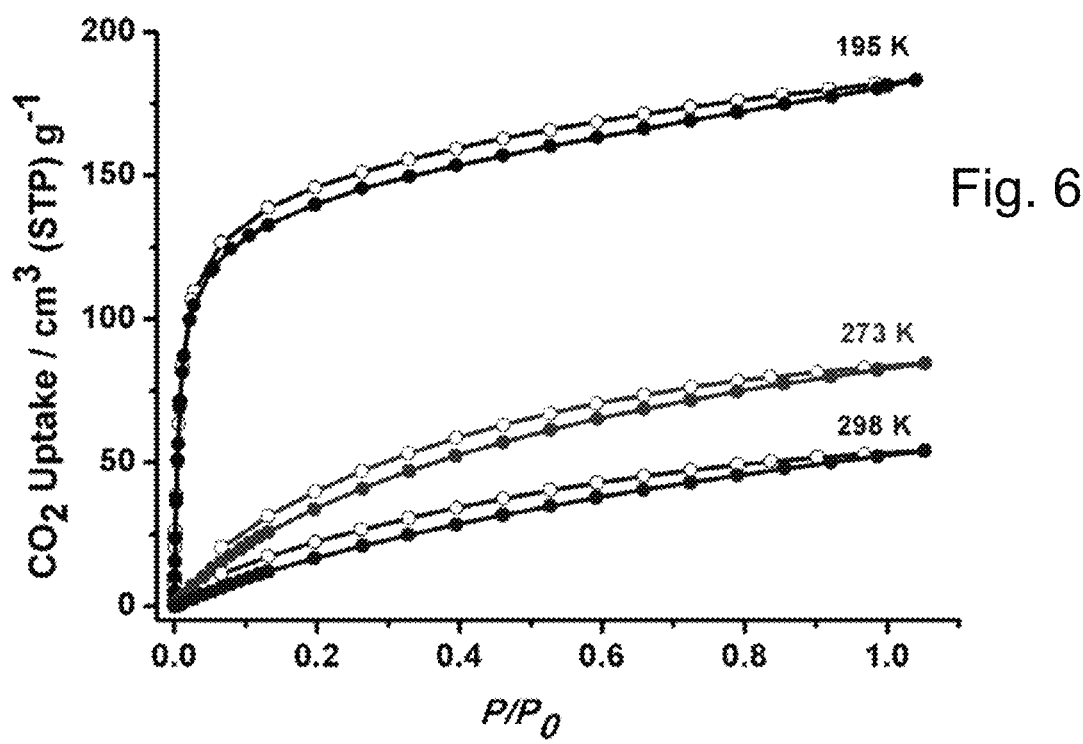
FIG. 6 shows CO$_2$ Adsorption (filled symbols) and desorption (open symbols) isotherms of SD 1•6AsF$_6$ at 195, 273 and 298 K.

The next level of the self-assembly process results (Level 3, FIG. 2A) in an unusual extended hierarchical superstructure. Ten noncovalently connected and vertex-sharing tetrahedral subunits assemble into one supramolecular diamondoid unit wherein an approximately spherical pore, of a 1.8 nm diameter, resides (FIG. 2A) at the center. After that, these diamondoid units (Level 3) assemble into the final hierarchical SD (Level 4, FIG. 2B), in which the extended packing (superstructure) is the same as that of natural diamond upon replacing the tetrahedral subunits (Level 2 assemblies) with $sp^3$-hybridized tetrahedral carbon atoms. It is noteworthy that SD is a 3D porous framework that possesses large and infinite channels containing type-III $PF_6^-$ counteranions. The channels arising from the diamondoid packing of the tetrahedral subunits exhibit (FIG. 2B) hexagonal windows with a diameter of ~1.0 nm. The type-III $PF_6^-$ anions and disordered solvent molecules scattered inside the channels make SD an excellent candidate for adsorbing guests. Meanwhile, MeCN molecules, type-II and III $PF_6^-$ anions form networks through multiple [C—H . . . F] interactions. Taking all the $PF_6^-$ counteranions into account, the 3D solvent accessible void fraction is as high as 52%, calculated geometrically[38] with a probe radius of 1.20 Å, in the activated superstructure (MeCN molecules were removed) with a total pore volume of 0.57 $cm^3$ $g^{-1}$. These values are comparable with other well-known supramolecular porous materials[33,39]. The total porosity of the superstructure was (FIGS. 5 and 6) also demonstrated by determining the $CO_2$ sorption isotherms.

Driving Forces and Electronic Band Gaps

In addition to unambiguously demonstrating the mechanism behind the formation of SD, further understanding at an atomic level is essential to obtain insight into the specificity of this hierarchical self-assembly and to guide future rational design. SCXRD Analysis and electronic property calculations reveal enormous differences in assembly behavior, which are ascribed to subtle variations in chemical compositions. Specifically, in contrast to the $D_{3d}$ doublesided tripodal conformation of 1•$6PF_6$, both the chloride and bromide salts of $1^{6+}$ crystallize in $C_{2v}$ symmetrical conformations with two pairs of arms up and two single arms down in an alternating manner. Although the intermolecular interactions ([C—H . . . N] and [π . . . π] stacking) still occur, the geometries of the superstructures of 1•6Br and 1•6Cl are entirely different from that of SD because of the lower symmetries of these conformations. In contrast, when the six arms are replaced with six 4-phenylpyridin-1-ium arms, which lead to the absence of [C—H . . . N] interactions between two arms from two adjacent molecules, a nonporous closely packed single-crystal superstructure represented by 2•$6PF_6$ forms. The single-crystal (super)structures of all these compounds, taken together, suggest that the preorganized $D_{3d}$ tripodal conformation of $1^{6+}$, the complementary intermolecular [C—H . . . N] interactions and the assistance of appropriate counteranions are used for the multivalent assembly of the $1^{6+}$ hexacation into an SD. Taking these design parameters into account, we expect that 1.6$AsF_6$ would assemble into an analog of SD and this expectation was indeed realized. The (super)structure of 1•6$AsF_6$ is (nearly the same as that of 1•$6PF_6$, an observation which highlights the fact that robust SD can be constructed with counteranions similar to $PF_6$. Using density functional theory (DFT), we predict the electronic band gap of 1•6$AsF_6$ to be almost the same as that of 1•$6PF_6$ at 3.76 and 3.65 eV, respectively using the B3LYP-D3 functional. The shift of −0.1 eV indicates primarily steric effects. We report the band gaps of 1•6Br and 1•6Cl, however, to be much narrower at 2.23 and 2.47 eV because of their lower symmetry compared with that of 1•$6PF_6$ and significantly different superstructures. The counteranion and the resultant geometry of the superstructure, therefore, can have a profound effect on the electronic properties (Table 1).

TABLE 1

Summary of single-crystal structural features and electronic band gaps.

| Compound | Crystallographic Parameters | | | | | DFT Calculation |
|---|---|---|---|---|---|---|
| | Crystal System | Space Group | a (Å) | b (Å) | c (Å) | Electronic Band Gap (eV) |
| 1 · $6PF_6$ | Cubic | Fd$\bar{3}$ | 39.35 | 39.35 | 39.35 | 3.65 |
| 1 · 6$AsF_6$ | Cubic | Fd$\bar{3}$ | 39.44 | 39.44 | 39.44 | 3.76 |
| 1 · 6Cl | Monoclinic | P2/c | 22.26 | 10.71 | 33.32 | 2.47 |
| 1 · 6Br | Hexagonal | $P6_222$ | 21.84 | 21.84 | 29.05 | 2.23 |

Size-Controllable and Straightforward Preparation

Figure 3A:
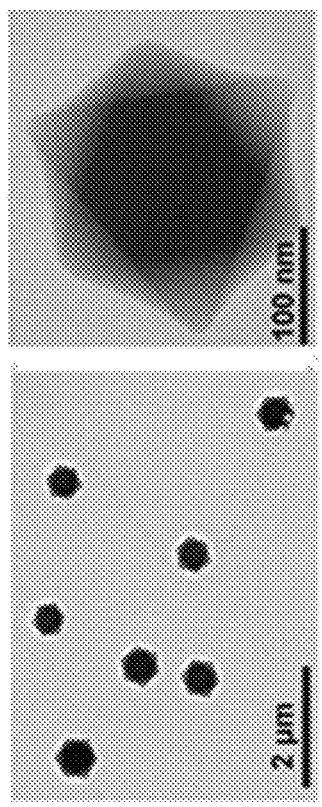
Figure 3B:
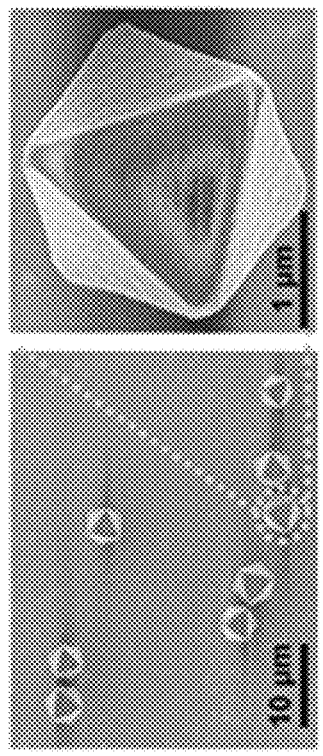
Figure 3C:
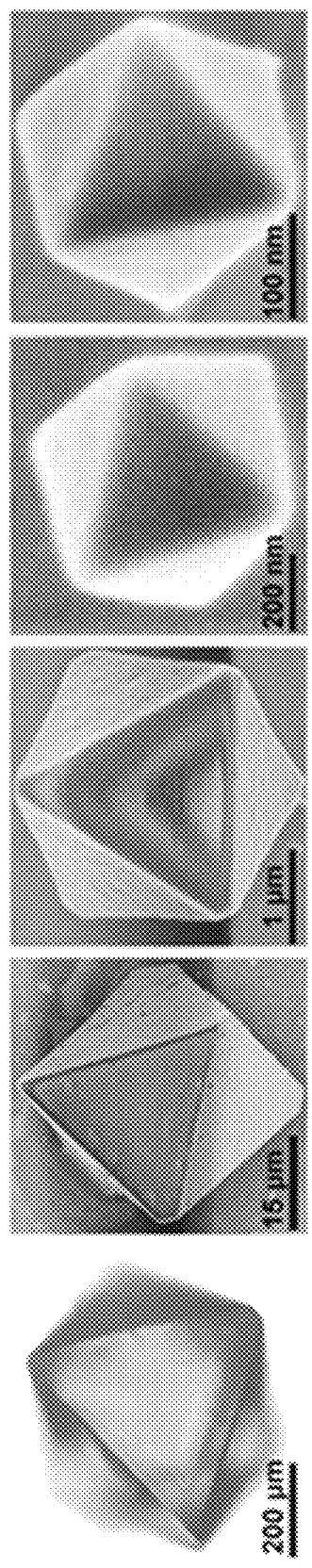
Figure 8:
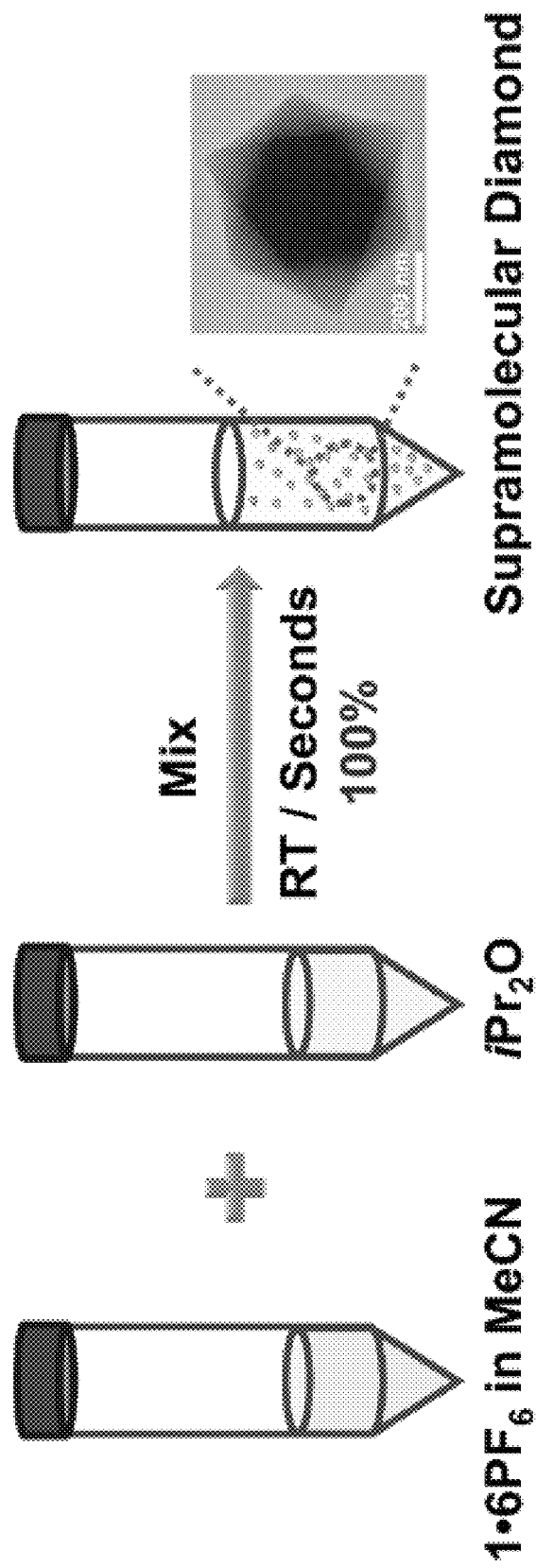
FIG. 8 shows schematic view of the preparation of SD 1•6PF$_6$ with sizes ranging from 280 nm to 3 µm.
Figure 9:
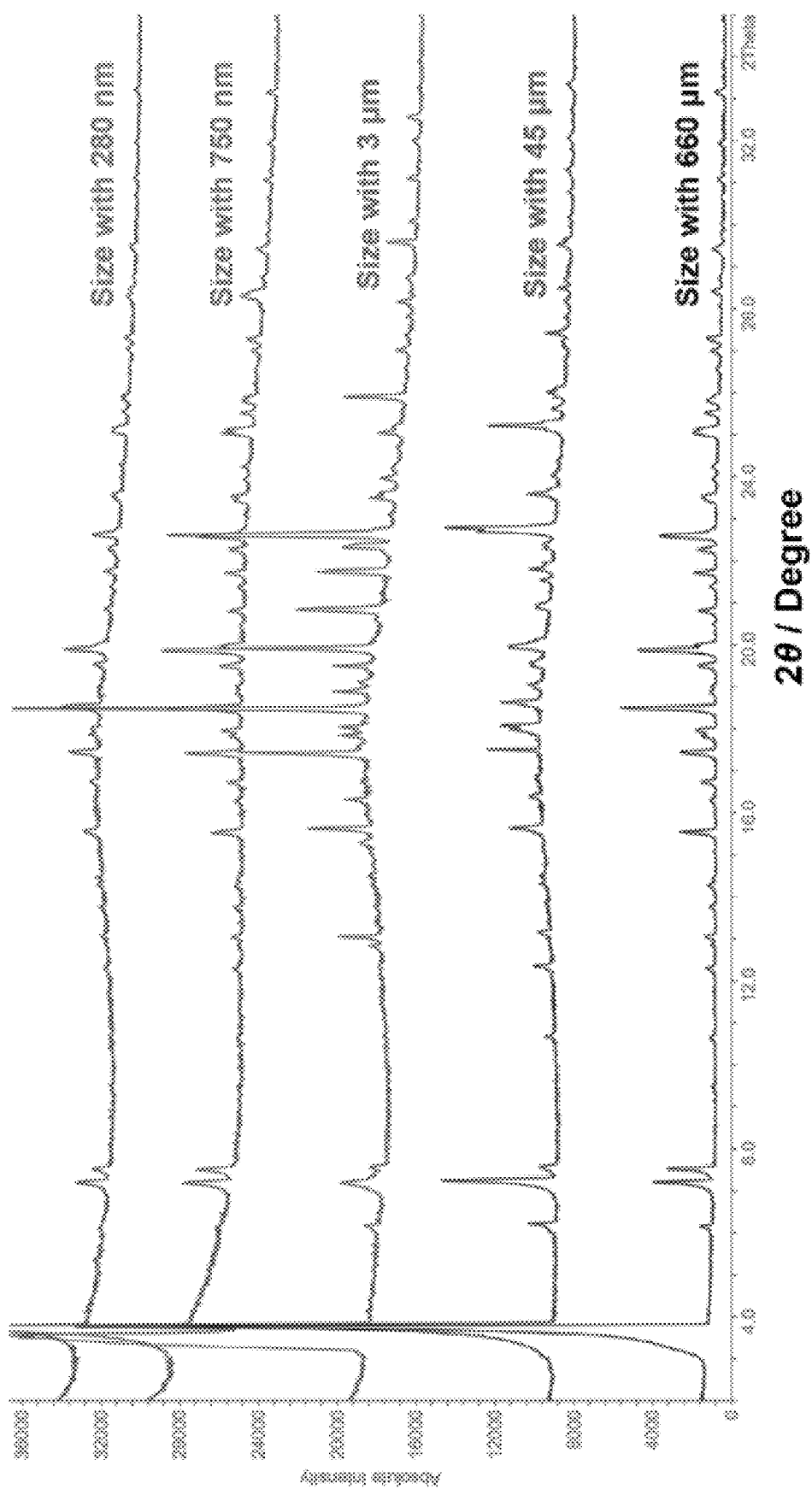
FIG. 9 shows a comparison of PXRD patterns of SD 1•6PF$_6$ with different sizes.
Figure 10:
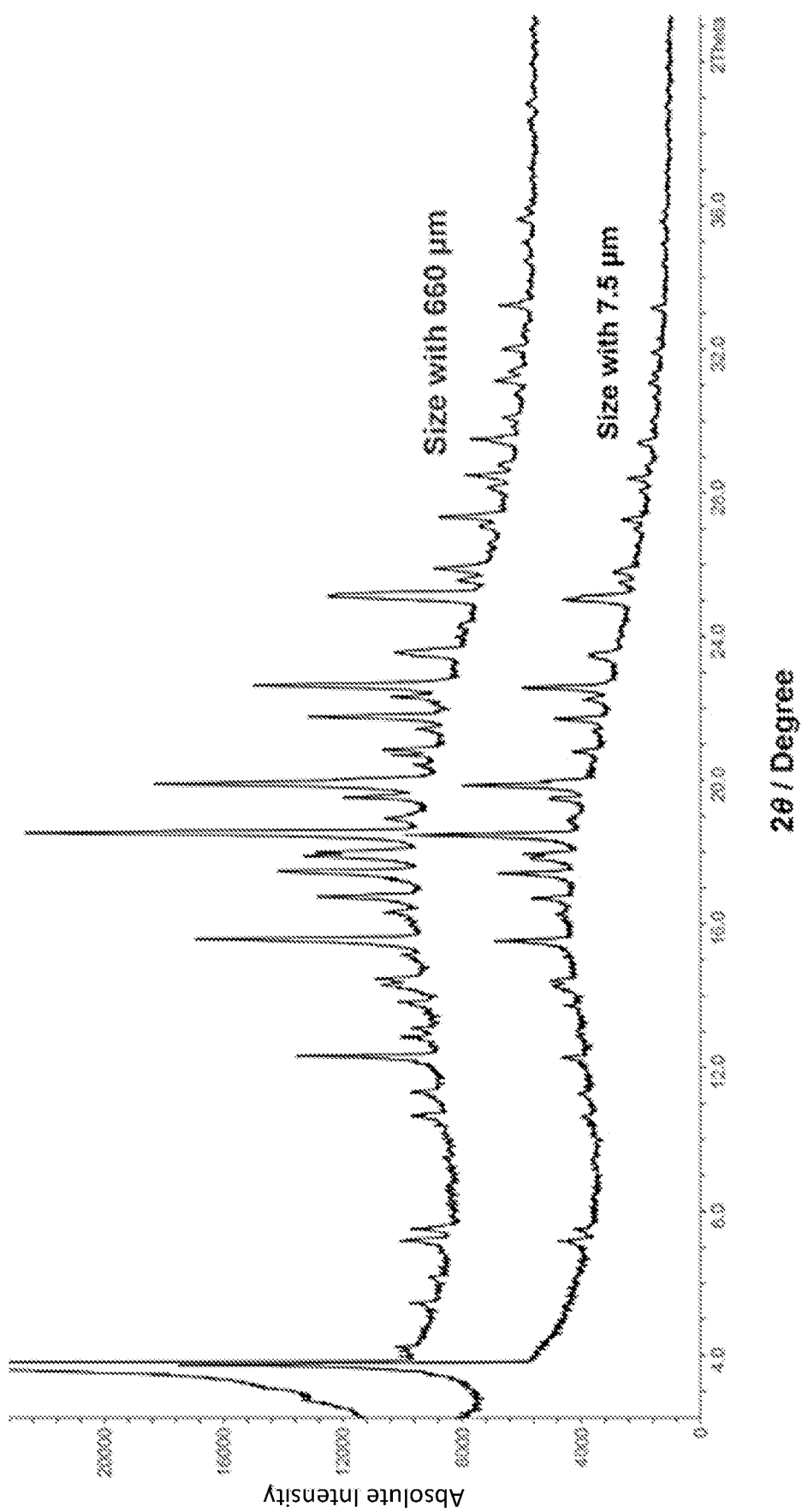
FIG. 10 shows a comparison of PXRD patterns of SD 1•6AsF$_6$ with different sizes.

Benefiting from the extraordinary efficiency and specificity of this spontaneous self-assembly, the preparation of SD is straightforward and controllable. Slow vapor diffusion of $iPr_2O$ (in 12 h) or diethyl ether ($Et_2O$ in 6 h) into a solution of 1•$6PF_6$ or 1•6$AsF_6$ in MeCN, affords (FIG. 7) single crystals with well-defined octahedral shapes and sizes of up to 45 μm (using $Et_2O$) and 660 μm (using $iPr_2O$). Notably, this crystallization can be carried out on a multi-gram scale. In addition, another more rapid and efficient method was also developed (FIG. 8) by adding $iPr_2O$ directly into solutions of 1•$6PF_6$ or 1•6$AsF_6$ in MeCN, which immediately leads to the quantitative production of regular octahedral crystals. Both SEM and TEM images indicate (FIGS. 3A and 3B) that the resulting precipitate is uniform octahedral SD. STEM equipped energy dispersive X-ray spectroscopy detector (STEM-EDS) maps show (FIGS. 3D and 3E) the homogeneity of the samples with all the component elements, which are evenly distributed throughout the crystals. More importantly, all the precipitated samples exhibit the same PXRD patterns (FIGS. 9 and 10) as that of the SD single crystals prepared by slow vapor diffusion. These observations indicate that the morphology and compositions, as well as the crystal superstructures of the samples, prepared by this rapid precipitation method, are identical to the aforementioned SD which is well-characterized by SCXRD. In addition, by employing this method, uniform octahedral crystals of SD, with controllable sizes ranging from 280 nm to 3 μm, can be prepared (FIG. 3C) easily within seconds by varying the concentration of 1•$6PF_6$ from 0.03 to 1.27 mM. The higher the concentration, the larger the crystals. This facile precipitation procedure, which modulates the size of SD varying from hundreds of nanometers to hundreds of micrometers, heralds its potential applications in nano- and optical devices[40].

Mobile Counteranions and Cationic Framework

The stability of the resulting SD samples of 1•$6PF_6$ and 1•6$AsF_6$ was confirmed by in situ variable-temperature (VT)

Figure 4A:
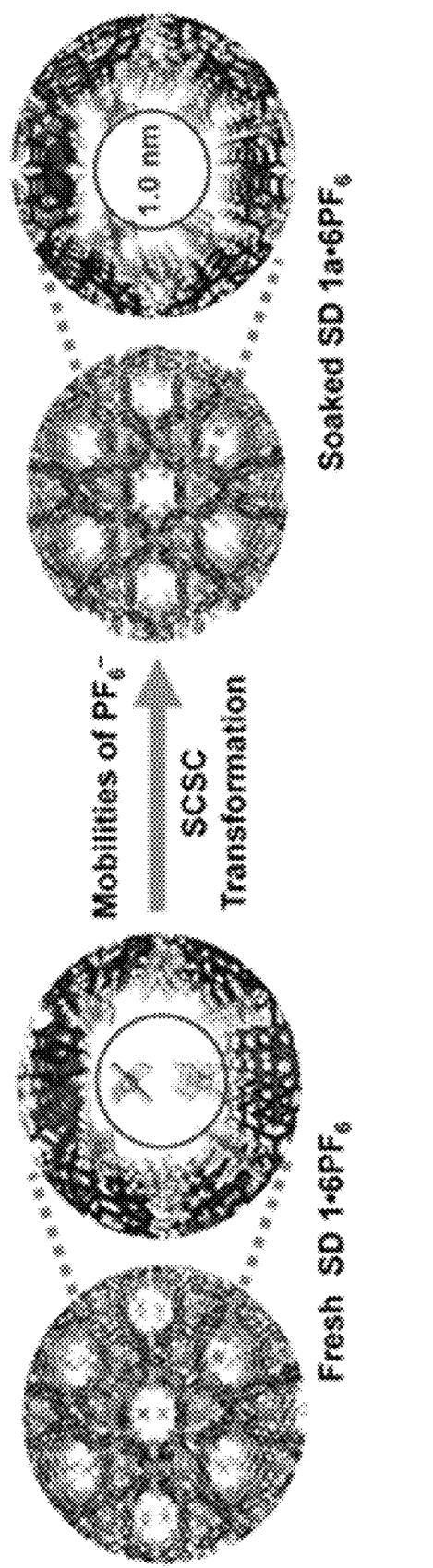
Figure 11:
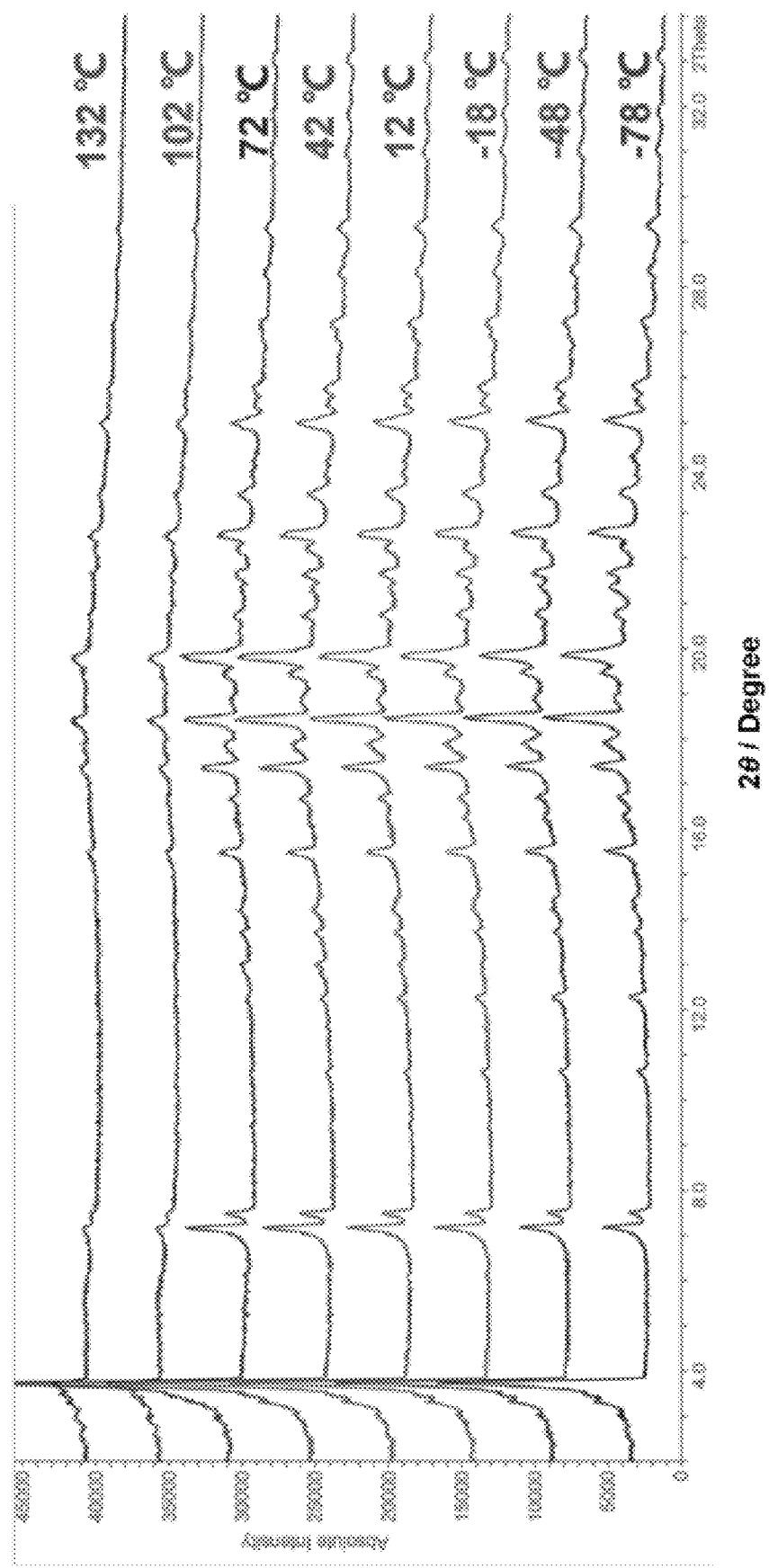
FIG. 11 shows VT-PRD patterns of SD 1•6PF$_6$.
Figure 12:
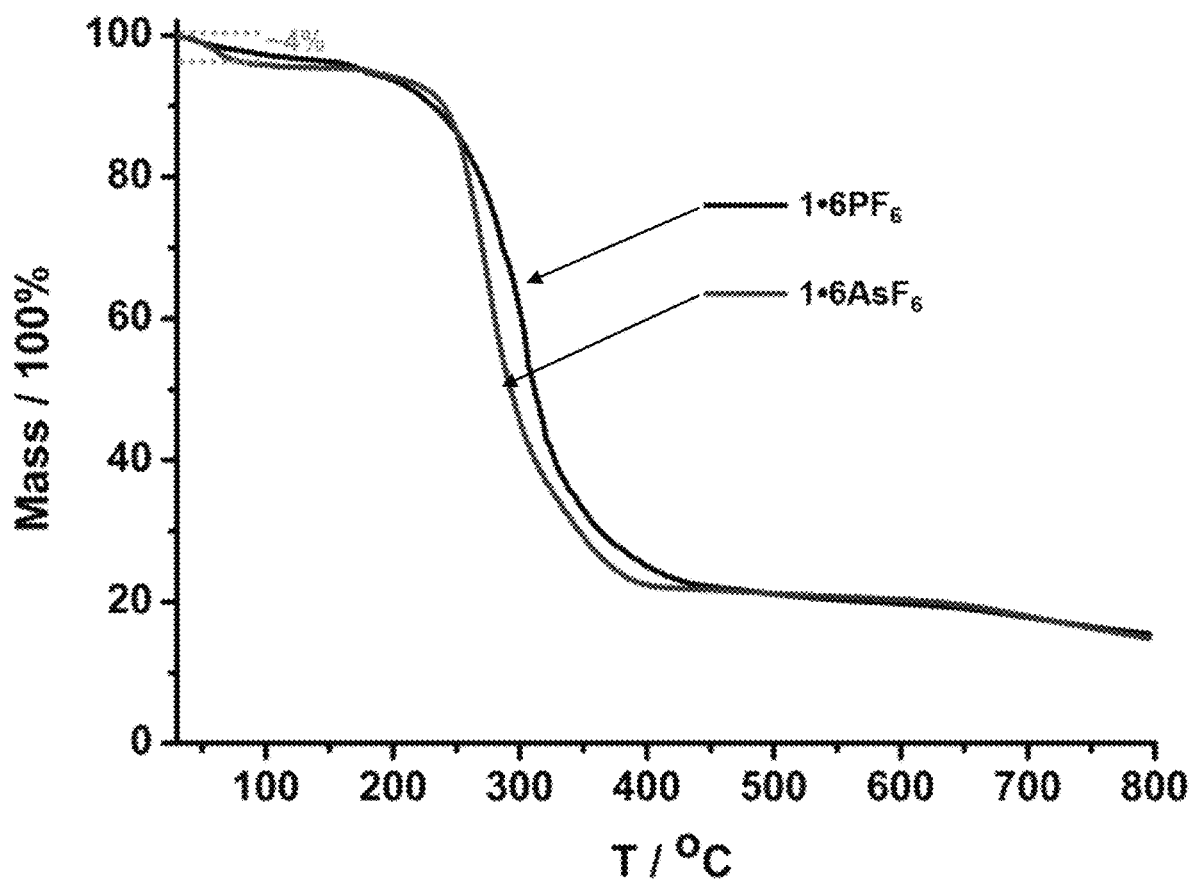
FIG. 12 shows TGA curves of 1•6PF$_6$ and 1•6AsF$_6$ under N$_2$.

PXRD analysis (FIG. 11) and thermogravimetric analysis (TGA) (FIG. 12). VT-PXRD indicates that the superstructure of SD is stable up to 100° C., while TGA reveals that the organic components themselves are stable up to 220° C. These observations highlight the robustness of the superstructure of SD. In addition, SD is extraordinarily stable in ethanol (EtOH) and isopropanol (iPrOH) even though both are good hydrogen bonding competitors with strong propensities for interfering with [C—H . . . F] and [C—H . . . N] interactions—the major driving forces for sustaining the superstructure of SD. Upon soaking SD in iPrOH for 7 days, the crystallinities are retained. SCXRD analysis (FIG. 4A) of SD 1a•6PF$_6$, soaked in iPrOH for 20 min, reveals that the space group, unit cell and the (super)structure of the cationic framework are to all intents and purposes the same as those from SD 1•6PF$_6$. A single-crystal-to-single-crystal (SCSC) transformation, however, occurs. In contrast to the anions present in SD 1•6PF$_6$, the positions and arrangements of sites with partially occupying by PF$_6^-$ anions in the soaked samples SD 1a•6PF$_6$ are different. The type-I PF$_6^-$ anions are located tightly in the cavities of the tetrahedra, while the type-II PF$_6^-$ anions associated with the faces of tetrahedra and type-III PF$_6^-$ located in the nanochannels are not in their original positions. The mobilities of these PF$_6^-$ anions result in more spacious nanoporosity (FIG. 4A) throughout the extended framework. Large numbers of supramolecular organic frameworks have been constructed in the last two decades[41]. Most of these materials, however, suffer the poor stability in solution and can only be used in the solid state. The robustness of SD in EtOH and iPrOH, thus, is unexpected and commendable.

Figure 13A:
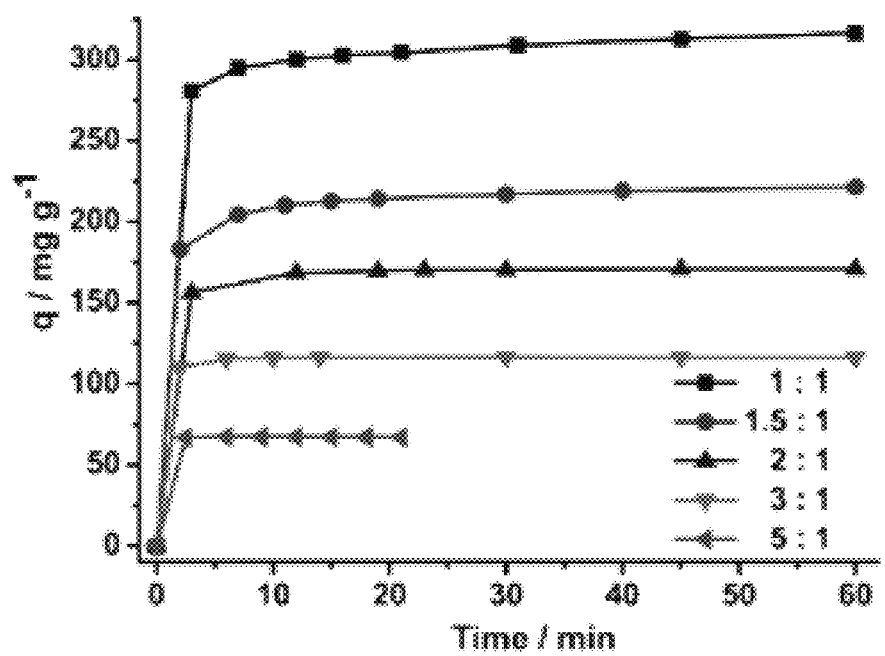
FIGS. 13A-13B.
Figure 13B:
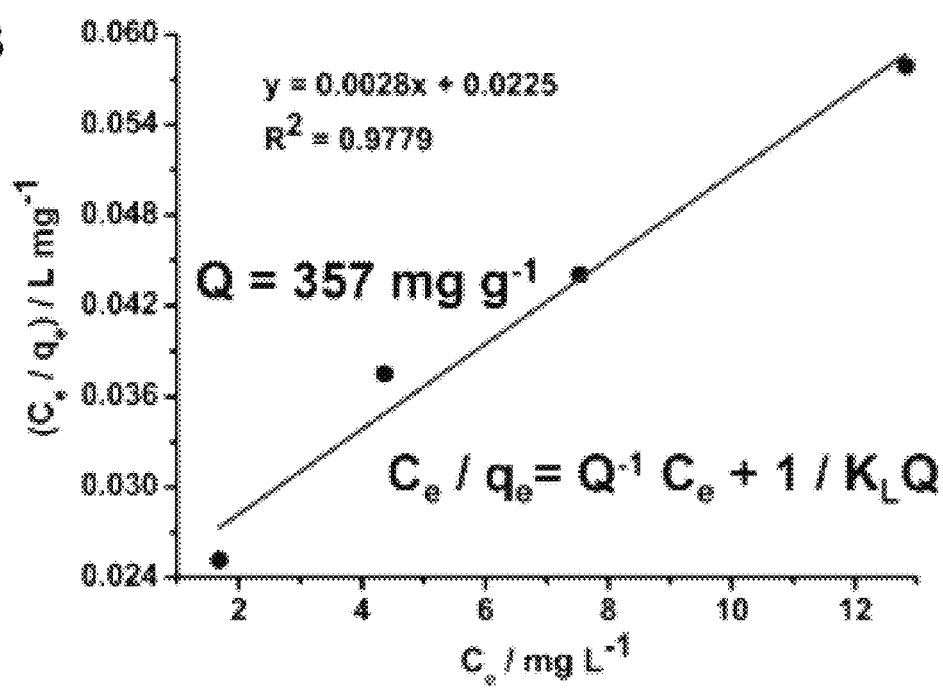
Figure 14:
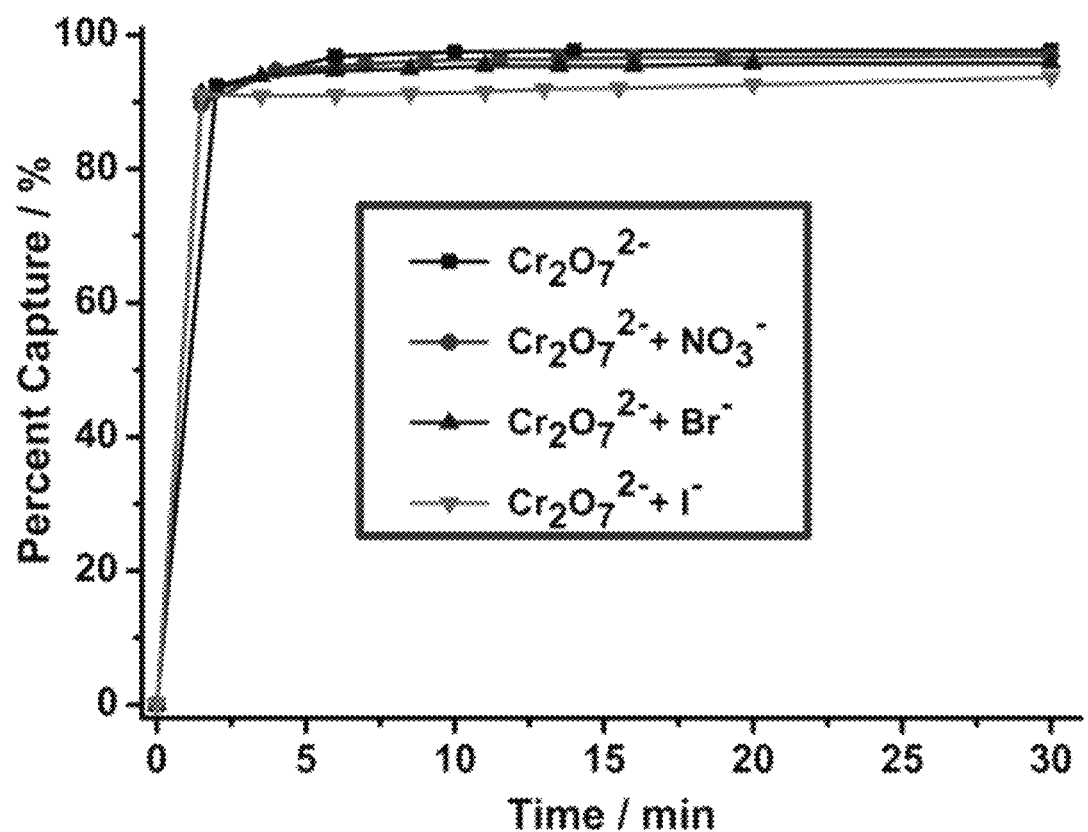
FIG. 14 shows the capture of Cr$_2$O$_7^{2-}$ as a percentage vs time from equimolar solutions of various ions (NO$_3^-$, Br$^-$ and I$^-$)

In order to confirm the mobilities of the type-II and -III anions and the 3D intrinsically cationic nanoporosity of SD, we carried out a series of counteranion exchange experiments with dichromate (Cr$_2$O$_7^{2-}$) dianions and perrhenate (ReO$_4^-$) anions. After soaking crystals of SD 1•6PF$_6$ (15 mg) in a solution (0.14 mM) of bis(tetrabutylammonium) dichromate ((Bu$_4$N)$_2$Cr$_2$O$_7$) in EtOH (10 mL), the process of anion exchange could be monitored by following the changes in the absorbance at 358 nm, where Cr$_2$O$_7^{2-}$ absorbs. The molar ratio of SD 1•6PF$_6$ to Cr$_2$O$_7^{2-}$ was 5:1 at the initial stage. Equilibrium was reached within 2 min, and 99% of the Cr$_2$O$_7^{2-}$ dianions in solution were exchanged into the SD crystals, as evidenced (FIG. 4B) by the decolorization of the supernatant solution. The maximum adsorption capacity for Cr$_2$O$_7^{2-}$ was (FIG. 13A-13B) determined to be 357 mg g$^{-1}$ by fitting the data with the Langmuir equation. In addition, SD maintains (FIG. 14) its fast kinetics and excellent capacity, even in the presence of equimolar amounts of nitrate or halides.

We also explored the exchangeability of SD toward ReO$_4^-$ which is widely recognized[42] as a good nonradioactive surrogate for the radioactive contaminant TcO$_4^-$. Under the same conditions—namely, soaking crystals of SD 1•6PF$_6$ (15 mg) in a solution (0.14 mM) of tetrabutylammonium perrhenate (Bu$_4$NReO$_4$) in EtOH (10 mL)—the sorption isotherm based on the inductively coupled plasma optical emission spectrometry (ICP-OES) measurement indicates (FIG. 4C) that 96% of ReO$_4^-$ was adsorbed into SD crystals within 2 min.

The adsorption kinetics observed here for both Cr$_2$O$_7^{2-}$ dianions[43] and ReO$_4^-$ anions[44] are among the fastest values compared with MOFs. The high capacities for Cr$_2$O$_7^{2-}$ dianions of 357 mg g$^{-1}$ [45] and ReO$_4^-$ anions of 220 mg$^{-1}$ [42,44] is also comparable with MOFs.

Figure 15A:
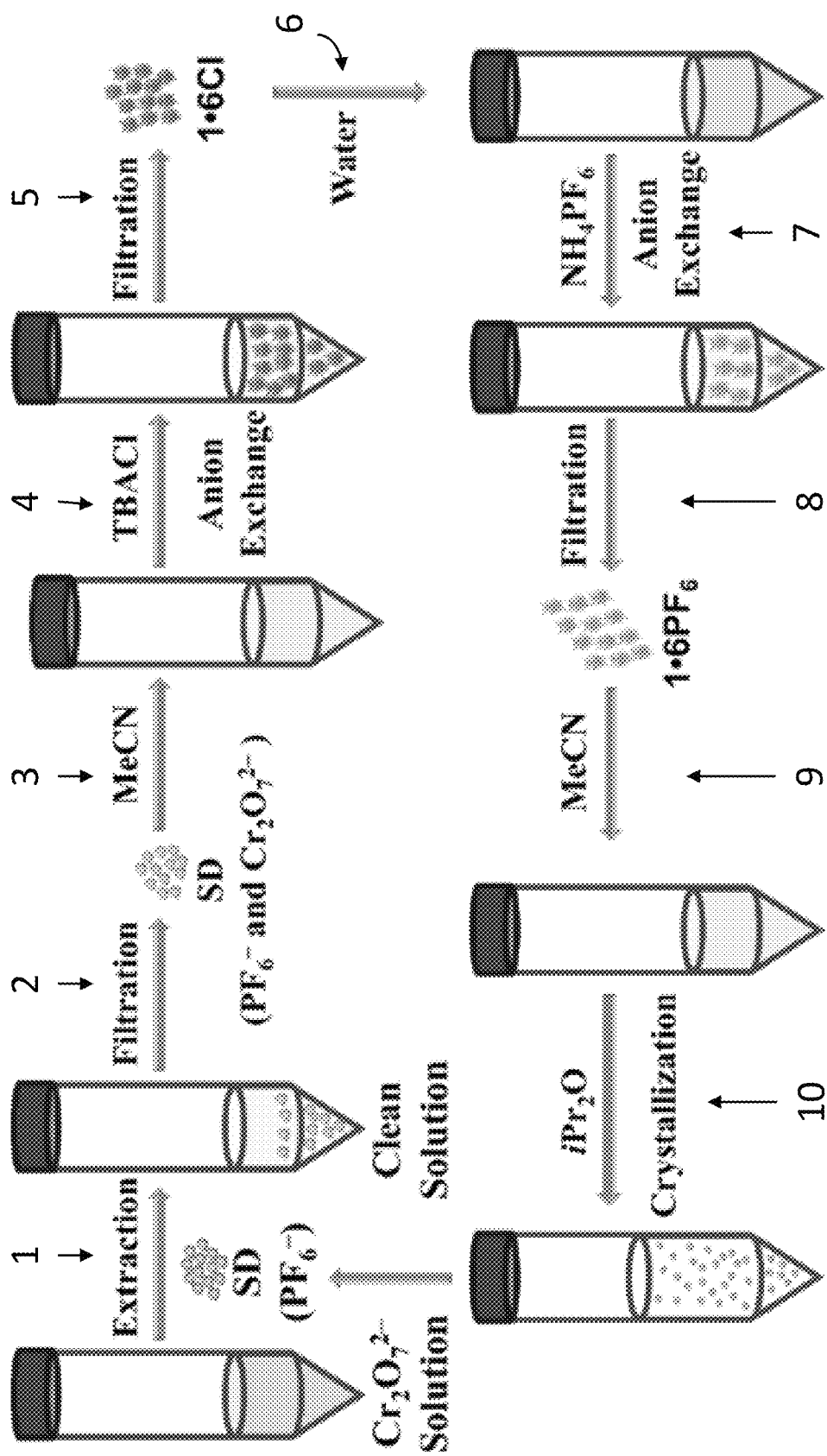
FIGS. 15A-15B.

More impressively, the original SD can be regenerated using a simple dissolution-repricipitation protocol (FIG. 15A) profiting from the reversible interaction in SD. An ionic contaminant may be extract 1 by contacting a solution comprising the ionic contamination, such as the oxoanion Cr$_2$O$_7^{2-}$, with the SD, such as 1•6PF$_6$. This will result in a clean solution and SD-bound contaminant because of anion exchange between the counterion of the SD and the ionic contaminant. The SD comprising the SD-bound contaminant by be filter 2 by any suitably method for separating solids from a liquid phase. The filtered SD be solubilized in a solvent 3, such as MeCN. An anion exchange salt, such as tetrabutylammonium chloride (TBACl), may be added to the SD solution, resulting in anion exchange 4 and precipitation such as described for the synthesis of 1•6Cl. The precipitate by be filtered 5 and solubilized in a solvent 6, such as water. A second anion exchange salt, such as NH$_4$PF$_6$ or NaAsF$_6$, may be added to the solution, resulting in anion exchange 7 and precipitation such as described for the synthesis of 1•6PF$_6$ or 1•6AsF$_6$. The precipitate, e.g., 1•6PF$_6$ or 1•6AsF$_6$, may be filtered 8 to isolate the precipitate. The precipitate, e.g., 1•6PF$_6$ or 1•6AsF$_6$, may undergo SCSC transformation by solubilizing the precipitate in a solvent 9, such as MeCN, and crystallizing the solution 10. This will result in the regeneration of SD for recycled use of the material to sequester ionic contaminant. Because of the stability of the SD in water, the fast kinetics and excellent efficiencies of all the counteranion exchanges, combined with the facile synthetic regeneration, allow SD to capture ionic contaminant such as hazardous metal oxoanions.

Figure 15B:
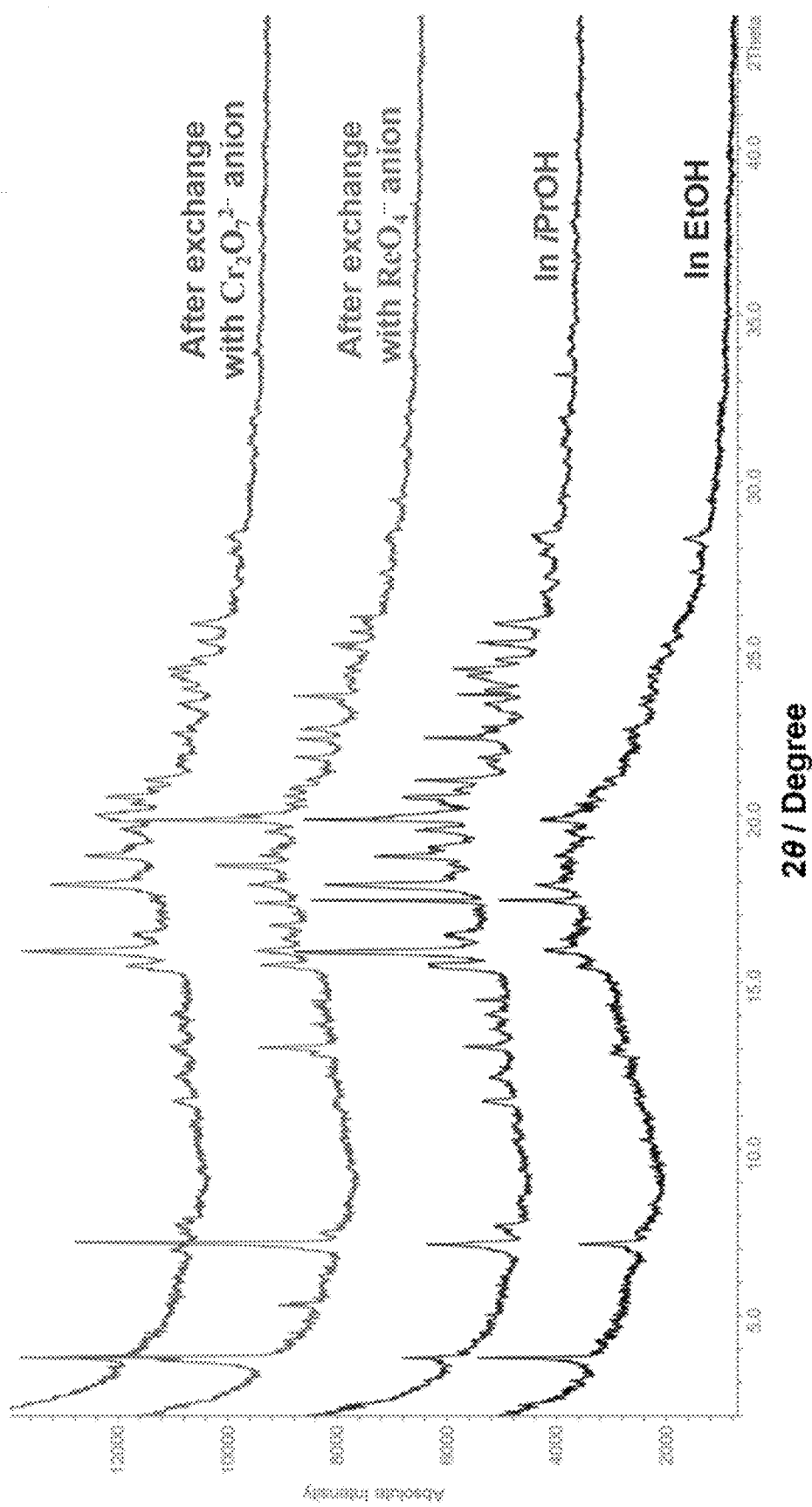
Figure 17A:
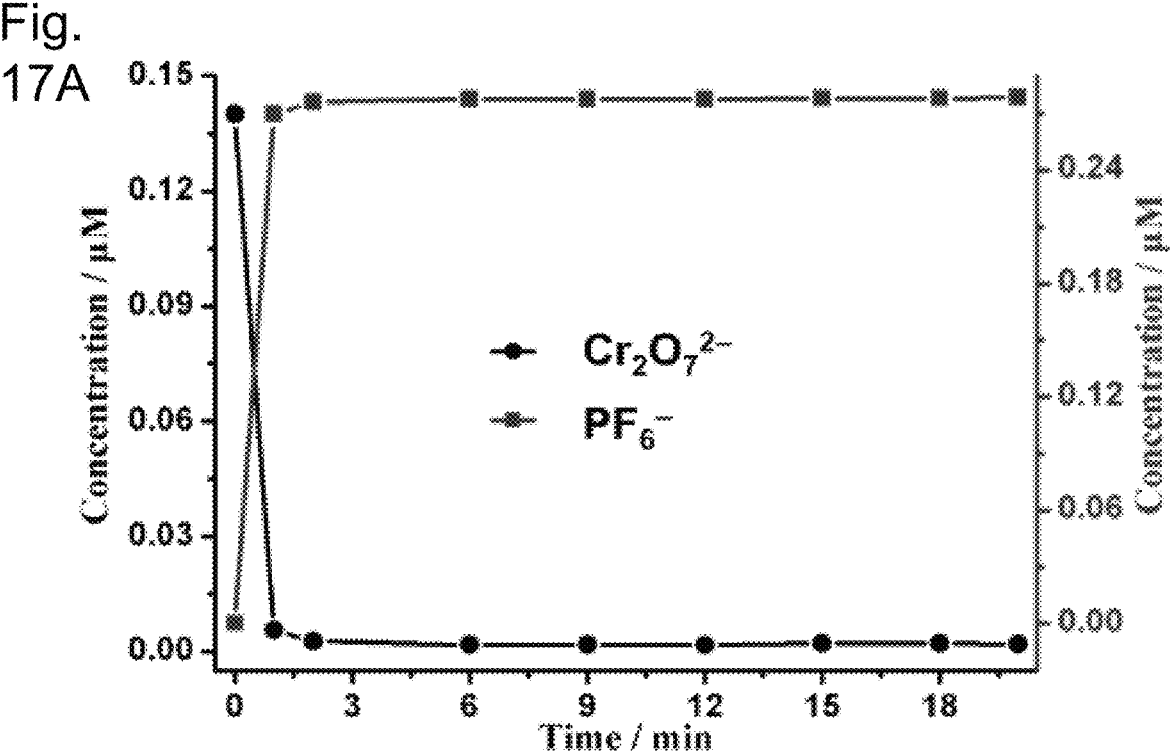
FIGS. 17A-17B.
Figure 17B:
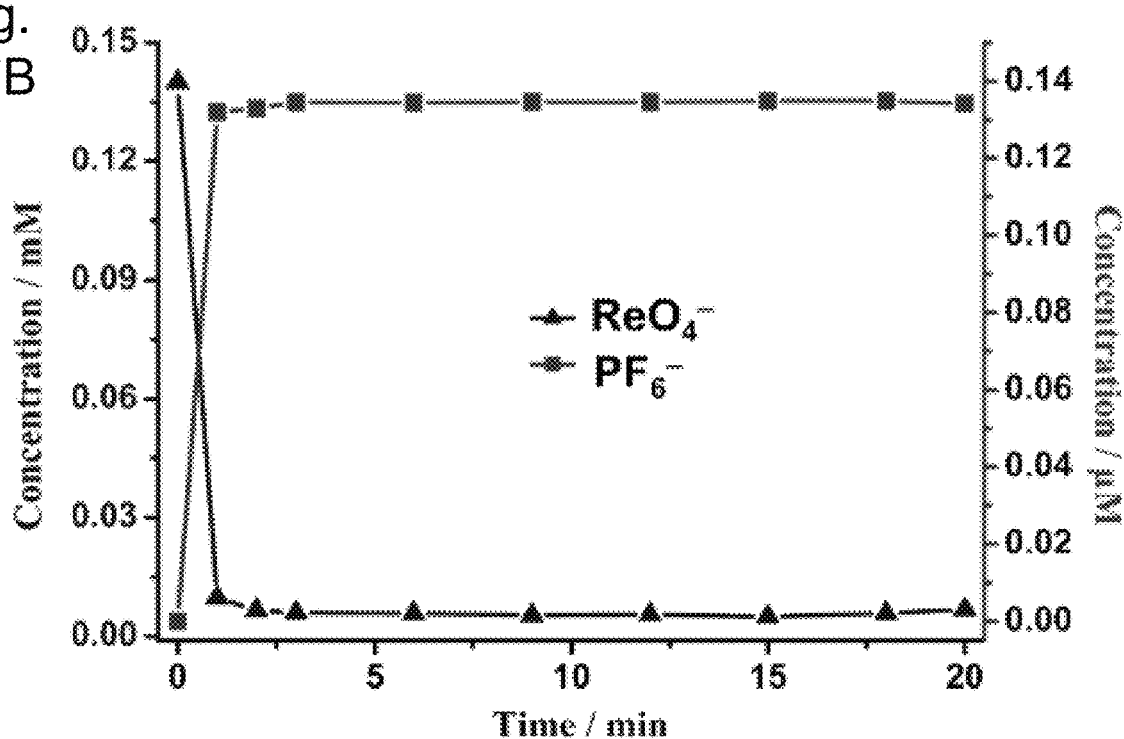
Figure 18:
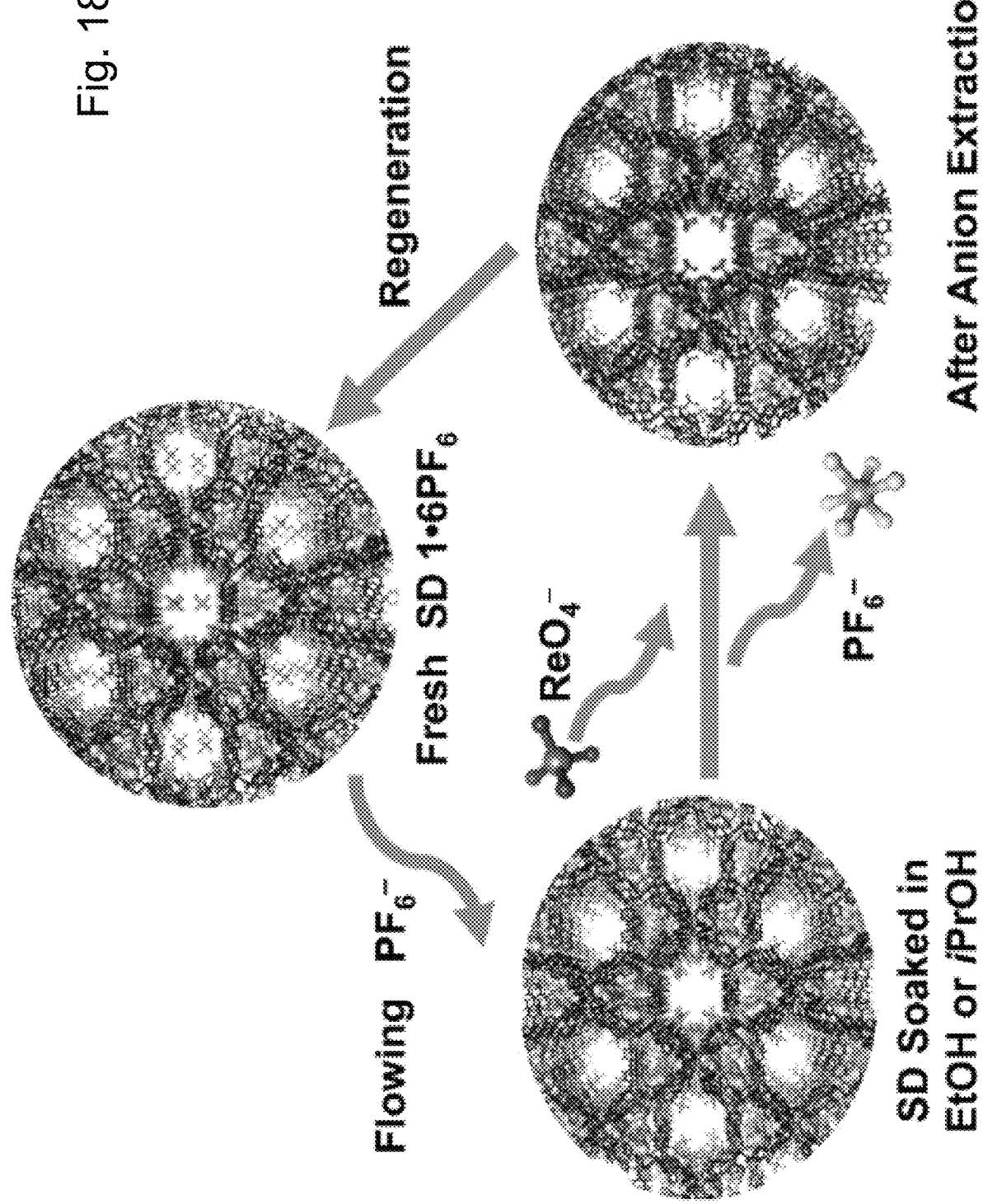
FIG. 18 shows the possible locations of PF$_6^-$ and ReO$_4^-$ in the SD 1•6PF$_6$ before and after anion extraction with ReO$_4^-$. The fixed PF$_6^-$ inside the truncated tetrahedral subunit were highlighted shown as space-filling representation, the organic skeletons as stick representation and movable PF$_6^-$ and ReO$_4^-$ as ball-stick representation.

After soaking in the solution of Cr$_2$O$_7^{2-}$ (12 equiv) or ReO$_4^-$ (12 equiv) for 2 h, the SD retains all the characteristics of the original SD in relation to shape, size, and crystallinity, as verified by STEM (FIGS. 4D and 4E) and PXRD (FIG. 15B). The encapsulation of Cr$_2$O$_7^{2-}$ and ReO$_4^-$ inside SD is in good agreement with the presence of chromium, oxygen and rhenium in the STEM-EDS maps of the exchanged crystals. Additionally, phosphorus and fluorine are still present in the exchanged crystals, implying that the exchange of the PF$_6^-$ anions in the framework is incomplete. During both anion exchanges, the counter cations of Bu$_4$N$^+$ are not able to enter the nanochannels of SD on account of both the Coulombic repulsive interactions and steric hindrance. This fact was verified by dissolving the exchanged SD crystals in CD$_3$CN. The $^1$H NMR spectrum of this solution shows no resonances (FIG. 16) arising from protons in the Bu$_4$N$^+$ cations. Meanwhile, 2 equiv or 1 equiv of PF$_6^-$ anions were exchanged into the solution of Cr$_2$O$_7^{2-}$ dianions or ReO$_4^-$ anion, respectively. The observations were verified by the increasing concentrations (FIGS. 17A-17B) of the phosphorus element based on the ICP-OES. Although SCXRD analyses could not be carried out as a result of the weak diffraction of the exchanged samples, the locations of the ReO$_4$ anions in the SD crystal structure were optimized using the molecular mechanics module in Materials Studio 7.0 (46), starting with the crystal structure of 1•6PF$_6$. The simulated superstructure reveals (FIG. 18) a plausible mechanism wherein the anion exchanged SD leads to the occupation of the mobile sites of type-II and -III PF$_6^-$ anions by ReO$_4$ anions, while the fixed type-I PF$_6^-$ anions stay inside the tetrahedral cages to support the overall superstructure. The driving forces for the efficient anion exchanges are the stronger hydrogen bonding interactions between the cationic fragments of SD and Cr$_2$O$_7^{2-}$/ReO$_4^-$ than those of PF$_6^-$.

SUMMARY

A hierarchical diamondoid superstructure—namely a supramolecular diamond (SD)—has been constructed efficiently by the tunable multivalent assembly of a highly symmetrical salt, hexakis[(4,4'-bipyridin-1-ium)methylene] benzene. The uniform crystalline samples can be prepared quantitatively in one-step within seconds under ambient conditions. The sizes of the resulting octahedral crystals can be modulated in the range of sub-micrometer to several hundred micrometers with the greatest of ease. The single-crystal X-ray diffraction and electronic band gap analyses make it possible to elucidate the mechanism and driving forces for the multivalent self-assembly. A single-crystal-to-single-crystal transformation reveals that the cationic framework of SD is extremely stable in the alcoholic solution while the counteranions are mobile in the channels. As a proof of its nanoporous characteristics and potential applications, the 3D supramolecular framework can remove efficiently $Cr_2O_7^{2-}$ and $ReO_4^-$ from the ethanol solutions. This research heralds a strategy for engineering complex supramolecular architectures from simple and symmetrical multi-charged molecules. This well-developed principle can be extended to other suitable (4,4'-bipyridin-1-ium)methylene benzene molecules.

Miscellaneous

No admission is made that any reference, including any non-patent or patent document cited in this specification, constitutes prior art. In particular, it will be understood that, unless otherwise stated, reference to any document herein does not constitute an admission that any of these documents form part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

General Procedure for Preparation of Single Crystals Suitable for X-Ray Crystallography Slow vapor diffusion of $iPr_2O$ or $Et_2O$ into solutions of 1•6Br or 1•6Cl in MeOH, 1•6PF$_6$, 1•6AsF$_6$ or 2•6PF$_6$ in MeCN, affords the single crystals suitable for X-ray crystallography after one day or two days. Single crystals of 1a•6PF$_6$ were obtained by soaking the single crystals of 1•6PF$_6$ in iPrOH for 20 min.

Calculations of Electronic Properties

The effect of the different charge-balancing anions and crystallographic structure on the electronic band gap was investigated using density functional theory (DFT) with the B3LYP-D3 functional.

General Procedure for the Size-Controllable Preparation of SD

Slow vapor diffusion of $iPr_2O$ in 12 h or $Et_2O$ in 6 h into a solution of 1•6PF$_6$ in MeCN, affords octahedral single crystals with sizes of 660 μm or 45 μm, respectively. To a solution of 1•6PF$_6$ or 1•6AsF$_6$ (5 mg) in MeCN (2 mL), 6 ml of $iPr_2O$ were added. Shake the mixture with hand to make the solution mix well. Precipitates with octahedral shapes and sizes of 3 μm were produced immediately. By varying the concentration of 1•6PF$_6$ from 0.03 to 1.27 mM, uniform crystals of SD with sizes ranging from 280 nm to 3 μm, were prepared.

General Procedure for Mobilities of Counteranions in SD

As-synthesized SD 1•6PF$_6$ (10 mg) with the size of 3 μm was immersed in a solution (10 mL) of $(Bu_4N)_2Cr_2O_7$ or $Bu_4NReO_4$ in EtOH, the resulting mixture was shaken gently at room temperature for 30 s. Ten 1.5-mL aliquots of the solution were transferred into 2-mL polypropylene centrifuge tubes at different time intervals (1, 2, 3, 5, 10, 15, 20, 25 and 30 min) and subjected to centrifugation at 12000 rpm for 30 s to allow separation of SD from the mixture. UV-vis spectroscopy or ICP-OES of the supernatant solution were recorded.

General Information

All commercially available reagents were used as received. Anhydrous acetonitrile and N,N'-dimethylformamide (DMF) were prepared using a solvent drying system. Hexamethylbenzene was synthesized according to the literatures[S1]. Nuclear magnetic resonance (NMR) spectra were recorded on Bruker Avance 500 spectrometers, with working frequencies of 500 MHz for $^1H$ and 125 MHz for $^{13}C$ nuclei, respectively. Chemical shifts were reported in ppm relative to the signals corresponding to the residual non-deuterated solvents ($CD_3SOCD_3$: $\delta_H$=2.50 and $\delta_C$=39.5 ppm; $CD_3CN$: $\delta_H$=1.94 and $\delta_C$=118.3 ppm). Abbreviations are used in the description of NMR spectroscopic data as follows: chemical shift (δ, ppm), multiplicity (s=singlet, d=doublet, t=triplet, m=multiplet), coupling constant (J, Hz). High-resolution mass spectra (ESI-HRMS) were measured on a Finnigan LCQ iontrap mass spectrometer. Single-crystal X-ray diffraction (SCXRD) data were collected on a Bruker APEX-II CCD diffractometer. Powder X-ray diffraction (PXRD) patterns were measured on an STOE-STADIMP powder diffractometer (Cu-Kα1 radiation, λ=1.54056 Å). Gas sorption isotherms were measured on a Micromeritics ASAP 2020 (Micromeritics, Norcross). Scanning electron microscopy (SEM) images were collected on a Hitachi SU8030 SEM. Scanning transmission electron microscopy (STEM) and energy dispersive X-ray spectroscopy (EDS) experiments were performed on a JEOL ARM300F GrandARM. Thermogravimetric analyses (TGA) were performed on a TGA/DCS 1 system. UV-Vis Absorption spectra were collected on a Shimadzu UV-3600 spectrophotometer to monitor the extraction progress of $Cr_2O_7^{2-}$ anions. Inductively coupled plasma optical emission spectrometry (ICP-OES) was performed on an Ultima2 spectrometer to monitor the anion extraction of $ReO_4^-$.

Synthetic Procedures

1. Synthesis of 1•6Br

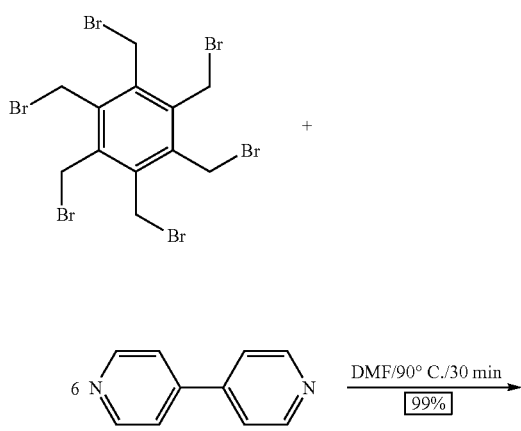

Scheme 1. Synthesis of 1•6Br

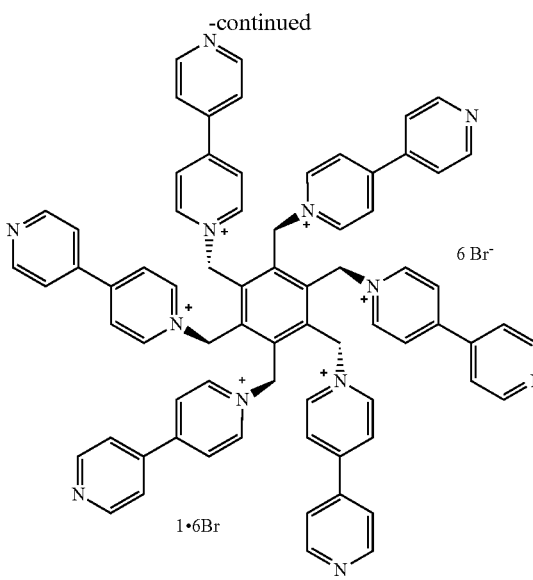

1·6Br

A solution of hexakis(bromomethyl)benzene (1.90 g, 3 mmol) in anhydrous DMF (30 mL) was added dropwise during 20 min to a solution of 4,4'-bipyridine (14.06 g, 90 mmol) in anhydrous DMF (100 mL) which was pre-heated to 90° C. The mixture was stirred continuously for 10 min at this same temperature. The resulting pale green precipitate was collected by filtration, washed with DMF (3×30 mL) and MeCN (3×30 mL), and dried to give the product (4.67 g, 2.97 mmol) in almost quantitative yield. $^1$H NMR (500 MHz, CD$_3$SOCD$_3$, 298 K) $\delta_H$=9.34 (d, J=4.99 Hz, 12H), 8.73 (d, J=4.94 Hz, 12H), 8.44 (d, J=4.94 Hz, 12H), 7.83 (d, J=4.99 Hz, 12H), 6.54 (s, 12H); $^{13}$C NMR (125 MHz, CD$_3$SOCD$_3$, 298 K) $\delta_C$=153.4, 151.4, 145.8, 140.5, 140.3, 125.7, 122.2, 58.0; ESI-HRMS Calcd for C$_{72}$H$_{60}$Br$_6$N$_{12}$: m/z=1491.0934 [M−Br]$^+$; found: 1491.0947 [M−Br]$^+$.

2. Synthesis of 1·6PF$_6$

Scheme 2. Synthesis of 1·6PF$_6$

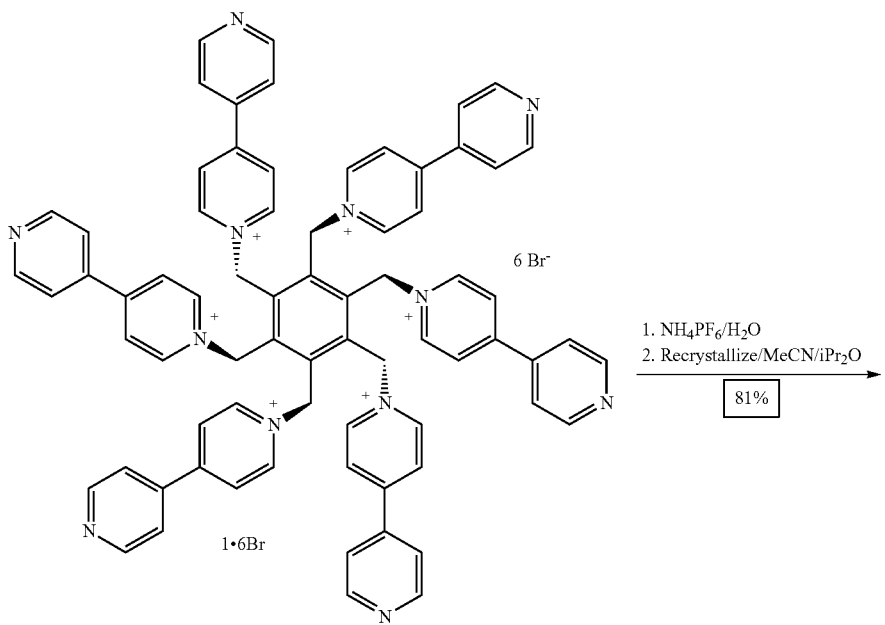

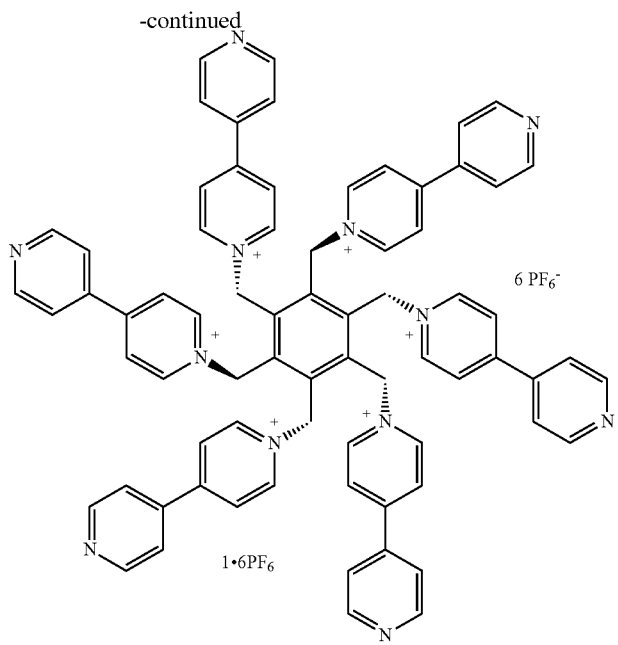

1•6PF₆

A solution of NH₄PF₆ (6.52 g, 40 mmol) in H₂O (10 mL) was added to a solution of 1•6Br (3.14 g, 2 mmol) in H₂O (0.1% TFA, 80 mL). The resulting pale green precipitate was collected by filtration, washed with H₂O (3×30 mL) and MeOH (3×30 mL), and dried. The remaining solid was recrystallized from MeCN and iPr₂O to afford 1•6PF₆ as a pale green crystalline solid (3.18 g, 1.62 mmol) in 81% yield. The analytically pure product was afforded as a white powder by high-performance reverse-phase preparative $C_{18}$ column chromatography. $^1$H NMR (500 MHz, CD₃CN, 298 K) $\delta_H$=8.80 (d, J=4.60 Hz, 12H), 8.60 (d, J=6.72 Hz, 12H), 8.32 (d, J=6.72 Hz, 12H), 7.71 (d, J=4.60 Hz, 12H), 6.02 (s, 12H); $^{13}$C NMR (125 MHz, CD₃CN, 298 K) $\delta_C$=156.9, 152.2, 145.2, 141.3, 140.9, 127.8, 122.7, 58.3; ESI-HRMS Calcd for $C_{72}H_{60}F_{36}N_{12}P_6$: m/z=1817.3267 [M−PF₆]⁺, 836.1810 [M−2PF₆]²⁺; found: 1817.3275 [M−PF₆]⁺, 836.1814 [M−2PF₆]²⁺.

3. Synthesis of 1•6Cl

Scheme 3. Synthesis of 1•6Cl

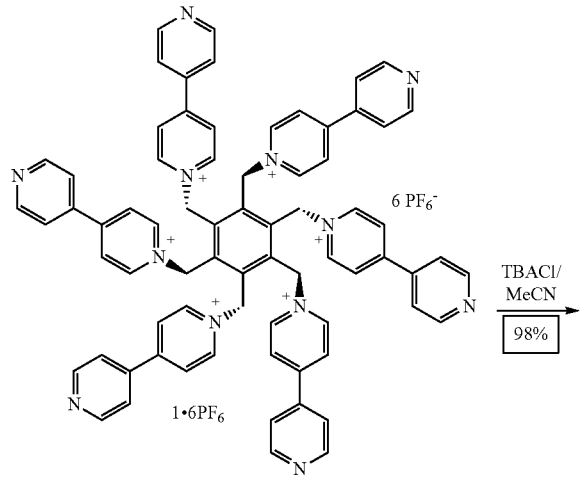

1•6PF₆

$\xrightarrow[\text{98\%}]{\text{TBACl/MeCN}}$

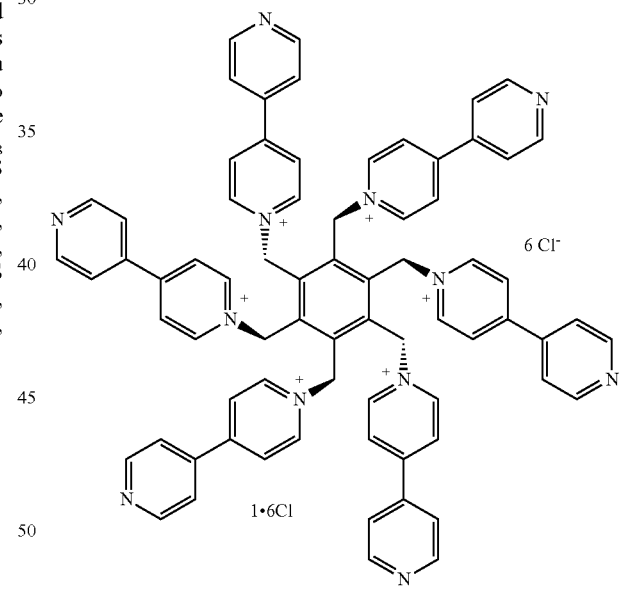

1•6Cl

A solution of tetrabutylammonium chloride (TBACl) (6.52 g, 40 mmol) in dry MeCN (5 mL) was added to a solution of 1•6PF₆ (196 mg, 0.1 mmol) in dry MeCN (10 mL). The resulting white precipitate was collected by filtration, washed with dry MeCN (3×5 mL), and dried to afford 1•6Cl as a white powder (128 mg, 0.098 mmol) in 98% yield. $^1$H NMR (500 MHz, CD₃OD, 298 K) $\delta_H$=9.34 (d, J=6.17 Hz, 12H), 8.73 (d, J=6.31 Hz, 12H), 8.50 (d, J=6.31 Hz, 12H), 7.84 (d, J=6.17 Hz, 12H), 6.61 (s, 12H); $^{13}$C NMR (125 MHz, CD₃OD, 298 K) $\delta_C$=155.9, 151.8, 146.8, 142.5, 142.1, 127.6, 123.4, 59.2; ESI-HRMS Calcd for $C_{72}H_{60}Cl_6N_{12}$: m/z=1269.3472 [M−Cl]⁺; found: 1269.3483 [M−Cl]⁺.

4. Synthesis of 1•6AsF$_6$

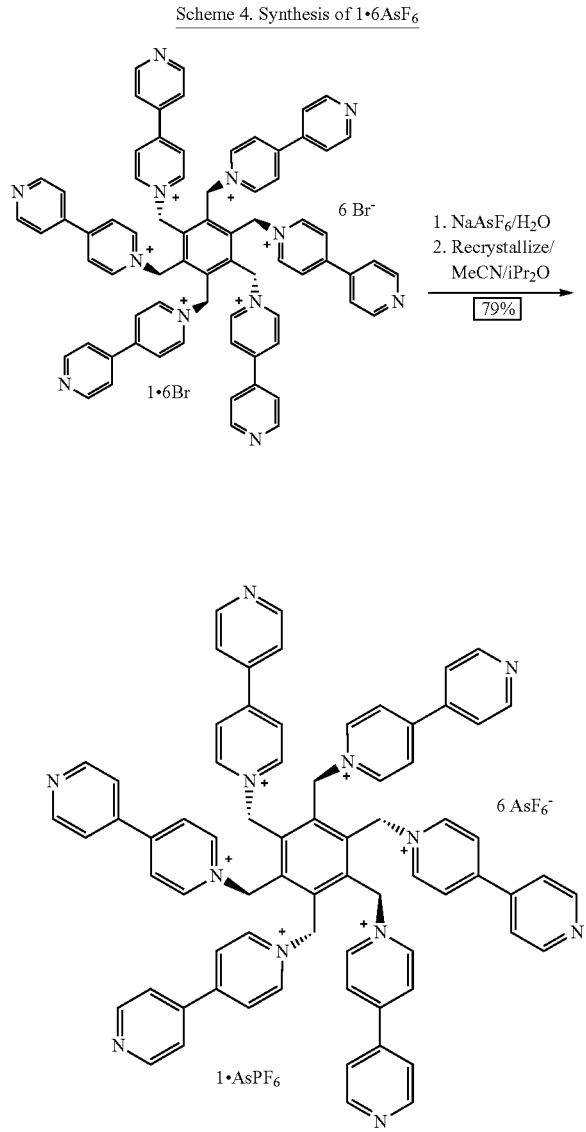

1•6AsF$_6$ was synthesized according to a procedure similar to that employed in the synthesis of 1•6PF$_6$. After anion exchange with NaAsF$_6$, 1•6AsF$_6$ was obtained as a pale green crystalline solid in 79% yield. The analytically pure product was isolated as a white powder by high-performance reverse-phase preparative C$_{18}$ column chromatography. $^1$H NMR (500 MHz, CD$_3$CN, 298 K)=8.80 (d, J=4.40 Hz, 12H), 8.58 (d, J=6.28 Hz, 12H), 8.32 (d, J=6.28 Hz, 12H), 7.67 (d, J=4.40 Hz, 12H), 6.00 (s, 12H); $^{13}$C NMR (125 MHz, CD$_3$CN, 298 K) $\delta_C$=157.0, 152.1, 145.1, 141.3, 141.1, 127.9, 122.8, 58.3; ESI-HRMS Calcd for C$_{72}$H$_{60}$As$_6$F$_{36}$N$_{12}$: m/z=2037.0659 [M–AsF$_6$]$^+$, 924.0767 [M–2AsF$_6$]$^{2+}$; found: 2037.0666 [M–2AsF$_6$]$^+$, 924.0773 [M–2AsF$_6$]$^{2+}$.

5. Synthesis of 2•6PF$_6$

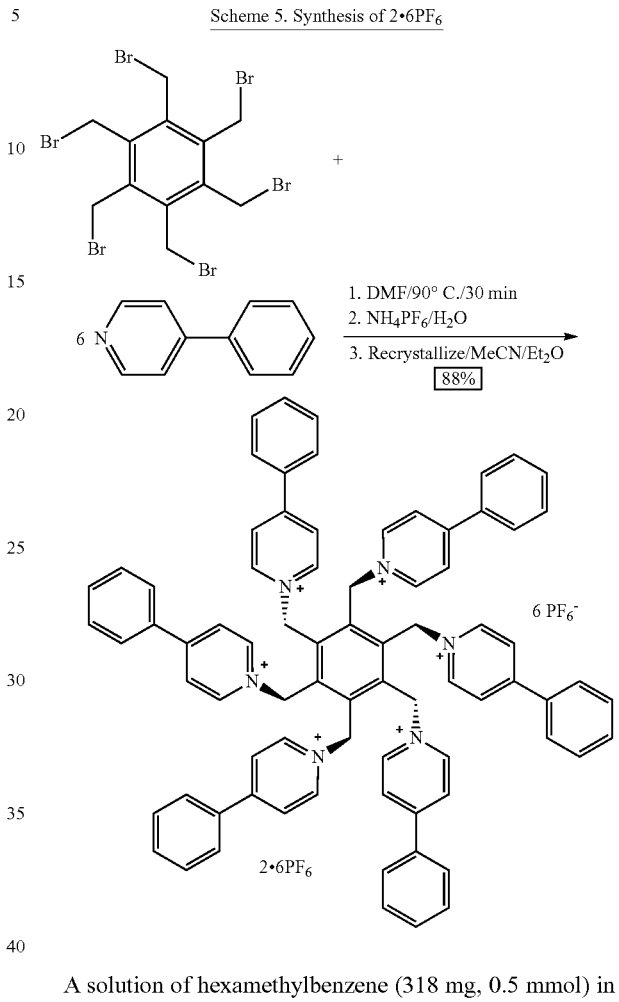

A solution of hexamethylbenzene (318 mg, 0.5 mmol) in anhydrous DMF (5 mL) was added dropwise during 20 min to a solution of 4-phenylpyridine (2.33 g, 15 mmol) in anhydrous DMF (15 mL) which was pre-heated to 90° C. The mixture was stirred at this same temperature for 3 h. The resulting pale yellow precipitate was collected by filtration, washed with DMF (3×10 mL) and MeCN (3×10 mL), and dried. The residue was dissolved in H$_2$O (20 mL). A solution of NH$_4$PF$_6$ (6.52 g, 40 mmol) in H$_2$O (3 mL) was added to the solution. The resulting pale yellow precipitate was collected by filtration, washed with H$_2$O (3×10 mL) and MeOH (3×10 mL), and dried. The solid was recrystallized from MeCN and Et$_2$O to afford 2•6PF$_6$ as a white crystalline solid (861 mg, 0.44 mmol) in 88% yield. $^1$H NMR (500 MHz, CD$_3$CN, 298 K) $\delta_H$=8.57 (d, J=6.60 Hz, 12H), 8.20 (m, J=6.60 Hz, 12H), 7.75 (d, J=8.46 Hz, 12H), 7.63 (t, J=8.46 Hz, 6H), 7.53 (m, 12H), 6.02 (s, 12H); $^{13}$C NMR (125 MHz, CD$_3$CN, 298 K) $\delta_C$=158.9, 144.6, 141.2, 134.1, 133.5, 130.8, 129.2, 126.6, 58.0; ESI-HRMS Calcd for C$_{78}$H$_{66}$F$_{36}$N$_6$P$_6$: m/z=833.1953 [M–2PF$_6$]$^{2+}$; found: 833.1946 [M–2PF$_6$]$^{2+}$.

X-Ray Crystallographic Characterization

Single crystals of 1•6PF$_6$ and 1•6AsF$_6$ were obtained after one day by slow vapor diffusion of iPr$_2$O into solutions of 1•6PF$_6$ or 1•6AsF$_6$ in MeCN, respectively. Single crystals of 1a•6PF$_6$ were obtained by soaking the single crystals of 1•6PF$_6$ in iPrOH for 20 min. Single crystals of 1•6Cl and 1•6Br were obtained after two days by slow vapor diffusion of iPr$_2$O into solutions of 1•6Br or 1•6Cl in MeOH, respectively. Single crystals of 2•6PF$_6$ were obtained after one day by slow vapor diffusion of Et$_2$O into a solution of 2•6PF$_6$ in MeCN. Single crystals suitable for X-ray crystallography were selected and mounted in inert oil and transferred to the cold N$_2$ gas stream of a Bruker Kappa APEX CCD area detector diffractometer. The crystals were kept at 100 K during data collection. Using Olex2$^{S2}$, data were resolved with the XM (1•6Br), XT (1•6Cl), ShelXS (1a•6PF$_6$, 2•6PF$_6$) or ShelXT (1•6PF$_6$, 1•6AsF$_6$)$^{S3}$ structure solution program depending on the structures and all are refined with the ShelXL$^{S4}$ refinement package using least squares minimization. When we refine the (super)structures of 1•6PF$_6$, 1a•6PF$_6$, 1•6AsF$_6$, 1•6Cl and 1•6Br, the solvent masking procedure as implemented in Olex2 was used to remove the electronic contribution of disordered solvent molecules from the refinement. As the exact solvent content is not known, only the atoms used in the refinement model are reported in the formula and the density was calculated without solvents. The crystallographic information, structural parameters for 1•6PF$_6$, 1a•6PF$_6$, 1•6AsF$_6$, 1•6Cl, 1•6Br, and 2•6PF$_6$ are as follows.

1•6PF$_6$ Crystal Data for C$_{84}$H$_{78}$F$_{36}$N$_{18}$P$_6$ (M=2209.46 g/mol): cubic, space group Fd$\bar{3}$ (no. 203), a=39.34860(10) Å, V=60923.9(5) Å$^3$, Z=16, T=99.85 K, μ(CuKα)=1.364 mm$^{-1}$, Dcalc=0.964 g/cm$^3$, 30649 reflections measured (3.89°≤2θ≤130.69°), 4228 unique (R$_{int}$=0.0276, R$_{sigma}$=0.0181) which were used in all calculations. The final R$_1$ was 0.1448 (I>2σ(I)) and wR$_2$ was 0.4532 (all data). Refinement model description. The enhanced rigid-bond restraint (SHELX keyword RIGU) was applied globally. The distances P3-F5, P3-F7, P3-F6, F5-F6, F5-F7 and F6-F7 were restrained. F6, P3, F5, and F7 were had restrained esds that their U$_{ij}$ components approximate to isotropic. P3, F5, F6, and F7 were had fixed Sof as 0.66667. Solvent Treatment Details. The solvent masking procedure, as implemented in Olex2, was used to remove the electronic contribution of disordered solvent molecules from the refinement. As the exact solvent content is not known, only the atoms used in the refinement model are reported in the formula here. Total solvent accessible volume/cell=25436.9 Å$^3$ [41.8%] Total electron count/cell=7703.7.

The solvent masking procedure, as implemented in Olex2, was used to remove the electronic contribution of disordered solvent molecules from the refinement. As the exact solvent content is not known, only the atoms used in the refinement model are reported in the formula here. Total solvent accessible volume/cell=35339.3 Å$^3$ [53.7%] Total electron count/cell=4400.5.

1•6AsF$_6$ Crystal Data for C$_{84}$H$_{78}$As$_6$F$_{36}$N$_{18}$ (M=2473.11 g/mol): cubic, space group Fd$\bar{3}$ (no. 203), a=39.44140(16) Å, V=61356.0(7) Å$^3$, Z=16, T=100.03 K, μ(CuKα)=2.145 mm$^{-1}$, Dcalc=0.964 g/cm$^3$, 25217 reflections measured (6.338°≤2θ≤136.356°), 4624 unique (R$_{int}$=0.0262, R$_{sigma}$=0.0193) which were used in all calculations. The final R$_1$ was 0.1309 (I>2σ(I)) and wR$_2$ was 0.4548 (all data). Refinement model description. The enhanced rigid-bond restraint (SHELX keyword RIGU) was applied globally. The distances As1-F1, As1-F2, As3-F5, As3-F6, As3-F7, F5-F6, F5-F7, and F6-F7 were restrained. As3, F5, F6, and F7 were had fixed Sof as 0.66667. Solvent Treatment Details. The solvent masking procedure, as implemented in Olex2, was used to remove the electronic contribution of solvent molecules from the refinement. As the exact solvent content is not known, only the atoms used in the refinement model are reported in the formula here. Total solvent accessible volume/cell=31936.1 Å$^3$ [52.1%] Total electron count/cell=6196.3.

1•6Cl Crystal Data for C$_{72}$H$_{60}$C$_{16}$N$_{12}$ (M=1306.02): monoclinic, space group P2/n (no. 13), a=22.661(3) Å, b=10.7083(15) Å, β=33.318(4) Å, 16=103.616(10°), V=7857.8(18) Å$^3$, Z=4, T=100.0 K, μ(CuKα)=2.343 mm$^{-1}$, Dcalc=1.104 g/mm$^3$, 5417 Fo>4sig (Fo) observed, 20632 reflections measured (5.458≤2θ≤117.86), 10873 unique (R$_{int}$=0.0948, R$_{sigma}$=0.1477) which were used in all calculations. The final R$_1$ was 0.1439 (I>2σ(I)) and wR$_2$ was 0.3637 (all data). Refinement Details. Rigid bond restraints were imposed on the displacement parameters as well as restraints on similar amplitudes separated by less than 1.7 Ang. globally. An idealized six-member ring was restrained on the N9a and N10a disordered rings. Solvent Treatment Details. The solvent masking procedure, as implemented in Olex2, was used to remove the electronic contribution of solvent molecules from the refinement. As the exact solvent content is not known, only the atoms used in the refinement

TABLE 2

| Atom names and symmetry codes of structure for hydrogen bonding. | | | | | | | |
|---|---|---|---|---|---|---|---|
| Atoms | F1 ... H3 | F1 ... H3 | F2 ... H4 | F4 ... H9 | F4 ... H10 | F5 ... H12 | F5 ... H12 |
| Distance (Å) | 2.27 | 2.33 | 2.56 | 2.50 | 2.62 | 2.57 | 2.67 |
| Symmetry code | 51_666 | 50_666 | 50_666 | 54_565 | 59_655 | 36_555 | I |
| Atoms | F3 ... H14A | F3 ... H14A | F6 ... H14C | N2 ... H2B | N2 ... H7 | N3 ... H2A | |
| Distance (Å) | 2.70 | 2.86 | 2.62 | 2.31 | 2.50 | 2.50 | |
| Symmetry code | I | 4_665 | I | 91_556 | 91_556 | I | |

1a•6PF$_6$ Crystal Data for C$_{72}$H$_{60}$F$_{36}$N$_{12}$P$_6$ (M=1963.14 g/mol): cubic, space group Fd$\bar{3}$ (no. 203), a=40.3697(7) Å, V=65791(3) Å$^3$, Z=16, T=99.96 K, μ(CuKα)=1.211 mm$^{-1}$, Dcalc=0.793 g/cm$^3$, 23577 reflections measured (7.262°≤2θ≤127.346°), 4536 unique (R$_{int}$=0.0717, R$_{sigma}$=0.0607) which were used in all calculations. The final R$_1$ was 0.1019 (I>2σ(I)) and wR$_2$ was 0.3450 (all data). Refinement model description. P2, F3, F4, F5, F6, F7 and F8 were had fixed Sof as 0.66667. Solvent Treatment Details.

model are reported in the formula here. Total solvent accessible volume/cell=1555.7 Å$^3$ [19.4%] Total electron count/cell=381.1.

1•6Br Crystal Data for C$_{72}$H$_{60}$Br$_6$N$_{12}$ (M=1572.78): hexagonal, space group P6222 (no. 180), a=21.836(4) Å, c=29.046(6) Å, V=11994(5) Å$^3$, Z=6, T=99.98 K, μ(CuKα)=3.971 mm$^{-1}$, Dcalc=1.306 g/mm$^3$, 3308 Fo>4sig (Fo) observed, 22723 reflections measured (4.672≤2θ≤88.982), 3125 unique (R$_{int}$=0.0488, $R_{sigma}$=0.0462) which were used in all calculations. The final $R_1$ was 0.1120 (I>2σ(I)) and $wR_2$ was 0.3562 (all data). Refinement Details. The enhanced rigid-bond restraint (SHELX keyword RIGU) was applied globally. All atoms were also had restrained esds that their $U_{ij}$ components approximate to isotropic. The phenylene rings were refined in idealized rings with an AFIX 66. Solvent Treatment Details. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=2386.2 Å$^3$ [19.9%] Total electron count/cell=718.4.

2•6PF$_6$ Crystal Data for $C_{86}H_{78}F_{36}N_{10}P_6$ (M=2121.40 g/mol): monoclinic, space group P2$_1$/c (no. 14), a=18.0319(4) Å, b=23.1962(5) Å, c=21.9244(5) Å, β=102.0070(13)°, V=8969.7(4) Å$^3$, Z=4, T=100.0 K, μ(CuKα)=2.262 mm$^{-1}$, Dcalc=1.571 g/cm$^3$, 81473 reflections measured (5.01°≤2θ≤136.688°), 16180 unique ($R_{int}$=0.0461, $R_{sigma}$=0.0349) which were used in all calculations. The final $R_1$ was 0.1007 (I>2σ(I)) and $wR_2$ was 0.2919 (all data). Refinement model description. Secondary CH$_2$ refined with riding coordinates. Aromatic H refined with riding coordinates. Idealized Me refined as a rotating group.

TABLE 3

Parameters of single crystals with various fragments and anions.

| Compound | Anion | Solvent | Space Group | Supramolecular Diamond |
|---|---|---|---|---|
| 1·6PF$_6$ | PF$_6^-$ | MeCN/iPr$_2$O | Fd$\bar{3}$ | Yes |
| 1a·6PF$_6$ | PF$_6^-$ | MeCN/iPr$_2$O/iPrOH | Fd$\bar{3}$ | Yes |
| 1·6AsF$_6$ | AsF$_6^-$ | MeCN/iPr$_2$O | Fd$\bar{3}$ | Yes |
| 1·6Cl | Cl$^-$ | MeOH/iPr$_2$O | P2/c | No |
| 1·6Br | Br$^-$ | MeOH/iPr$_2$O | P6$_2$22 | No |
| 2·6PF$_6$ | PF$_6^-$ | MeOH/Et$_2$O | P2$_1$/c | No |

DFT Calculations and Electronic Properties

The effect of the different charge-balancing anions and crystallographic structure on the electronic band gap was investigated using density functional theory (DFT). The band gap values reported are for the lowest energy ordered superstructures derived from the experimentally disordered CIF files. For example, to obtain the lowest energy ordered structures all plausible orientations of the partially-occupied anionic sites were considered, and the geometries were optimized with the corresponding symmetries for the superstructures. For 1•6PF$_6$ and 1•6AsF$_6$, the symmetry was reduced from Fd$\bar{3}$ (203) to the subclass F23 (196) while maintaining cubic symmetry. The ordered superstructures of 1•6Br and 1•6Cl have P6$_2$22 (180) and P2/c (13) symmetry respectively. The experimentally disordered geometry of 1•6Cl is P2/n which is a different cell setting of the same space group (13), which has been transformed in Table 6 for clarity in the comparison.

The DFT calculations were performed using the periodic ab initio CRYSTAL17 code[S5, S6]. The B3LYP[S8-S10] hybrid exchange-correlation functional was used with a semiempirical dispersion correction (B3LYP-D3)[S8-S10]. Each calculation was performed with all-electron atom-centered Gaussian-type basis sets of double-zeta quality for hydrogen, carbon, nitrogen, and fluorine, similar to previous work on the electronic properties of MOF$_S$[S11]. In order to ensure consistent and accurate treatment of the anions, triple-zeta valence basis sets with polarization reported by Peintinger et al[S12]. were used for phosphorus, chlorine, arsenic, and bromine.

The all-electron basis sets for the structures containing PF$_6^-$, AsF$_6^-$, Br$^-$ and Cl$^-$ contained a total of 8,304, 8,760, 10,332 and 6,432 basis functions, corresponding to 3,960, 4,392, 4,716 and 2,712 electrons spread over 2,880, 3,000, 3,636 and 2,304 shells per unit cell, respectively. The lattice parameters and atomic coordinates for all structures were optimized while maintaining the space group symmetry of each superstructure via a quasi-Newtonian algorithm[S13-S16]. The optimization of each geometry was considered to have converged when the maximum and root-mean-square (RMS) gradient, and the maximum and RMS atomic displacements were simultaneously below 4.5×10$^{-4}$, 3.0×10$^{-4}$, 1.8×10$^{-3}$ and 1.2×10$^{-3}$ a.u., respectively.

Summarized below are the comparisons of lattice parameters calculated from DFT (for ideal crystalline structures) with the experimental values.

TABLE 4

Comparison of the DFT and experimental lattice parameters for 1·6PF$_6$.

| Method | Lattice parameters (Å) a |
|---|---|
| Experimental | 39.349 |
| B3LYP-D3 | 38.601 |

The average difference in experimental and theoretical lattice parameters: 1.90%

TABLE 5

Comparison of the DFT and experimental lattice parameters for 1·6AsF$_6$.

| Method | Lattice parameters (Å) a |
|---|---|
| Experimental | 39.441 |
| B3LYP-D3 | 38.897 |

The average difference in experimental and theoretical lattice parameters: 1.38%

TABLE 6

Comparison of the DFT and experimental lattice parameters for 1·6Br.

| Method | Lattice parameters (Å) | |
|---|---|---|
| | a | c |
| Experimental | 21.836 | 29.046 |
| B3LYP-D3 | 21.312 | 29.459 |

The average difference in experimental and theoretical lattice parameters: 1.91%

TABLE 7

Comparison of the DFT and experimental lattice parameters for 1·6Cl.

| Method | Lattice parameters (Å) | | | |
|---|---|---|---|---|
| | a | b | c | β |
| Exp. P2/n | 22.661 | 10.708 | 33.318 | 103.616 |
| Exp. P2/c | 33.318 | 10.708 | 35.610 | 141.796 |
| B3LYP-D3 | 32.294 | 10.104 | 34.636 | 144.787 |

The average difference in experimental and theoretical lattice parameters: 3.39%

In order to investigate the effect of the (super)structure on the electronic band gap, we optimized the geometry of monoclinic and hexagonal superstructures, while exchanging the halides present in each superstructure. The DFT results from the hypothetical structures were encouraging, as the electronic band gaps did not change significantly. A slight decrease (−0.07 eV) in the value when $Br^-$ was replaced with $Cl^-$ was observed in the hexagonal superstructure, indicating purely steric changes, as reported in the main text for 1•6$PF_6$ and 1•6$AsF_6$. In the other exchange example where $Cl^-$ was replaced with $Br^-$ in the monoclinic superstructure, the band gap also decreased. The decrease partially resulted from fewer symmetry constraints in the monoclinic space group allowing the geometry to optimize to a structure closer to 1•6Br and hence the band gap value is almost identical (within 0.04 eV of 1•6Br). $PF_6^-$ and $AsF_6^-$ were not exchanged into the monoclinic and hexagonal superstructures, as the steric differences modified the chemical environment significantly. For completeness, the exchange of both halides into the highly ordered cubic superstructure of 1•6$PF_6$ was investigated and a lattice contraction (Table 8) was observed: very narrow band gaps comparable to semi-conductors were computed. The values for the exchanged anion geometries are computed for hypothetical structures but highlight the interesting electronic properties and the influence of the anion and superstructure. All electronic band gap values discussed are reported in Table 7.

TABLE 8

Summary of the electronic properties predicted for different superstructures.

| Anion | Electronic Band Gap (eV) | | |
|---|---|---|---|
|  | Cubic | Hexagonal | Monoclinic |
| $PF_6^-$ | 3.65 | — | — |
| $AsF_6^-$ | 3.76 | — | — |
| $Br^-$ | 1.04 | 2.23 | 2.19 |
| $Cl^-$ | 1.26 | 2.16 | 2.47 |

TABLE 9

Comparison of the DFT lattice parameters for cubic superstructures.

| Anion | Lattice parameters (Å) a |
|---|---|
| $PF_6^-$ | 38.601 |
| $AsF_6^-$ | 38.897 |
| $Br^-$ | 37.624 |
| $Cl^-$ | 37.371 |

$Cr_2O_7^{2-}$ Dianion

In a typical experiment, 15 mg of as-synthesized SD 1•6$PF_6$ with the size of 3 μm was immersed in a solution (10 mL) of $(Bu_4N)_2Cr_2O_7$ in EtOH (molar ratios of SD 1•6$PF_6$ to $Cr_2O_7^{2-}$ ranging from 0.17:1, 1:1, 1.5:1, 2:1, 3:1, and 5:1, respectively), and the resulting mixture was shaken gently at room temperature for 30 s. Seven 1.5-mL aliquots of the solution were transferred into 2-mL polypropylene centrifuge tubes at different time intervals (2, 5, 10, 15, 20, 25 and 30 min) and subjected to centrifugation for 30 s to allow separation of SD from the mixture. A 1.0-mL aliquot of the supernatant was decanted for monitoring the concentration of $Cr_2O_7^{2-}$ by UV-Vis spectroscopy on the basis of the typical absorption of $Cr_2O_7^{2-}$ anion at 358 nm. After each measurement, the solution was transferred back into the original vial in order to avoid any loss of the sample. The anion extraction capacity of SD was evaluated by measuring the decolorization rate of $Cr_2O_7^{2-}$ solution, which was calculated by the following eq 1:

$$D = \frac{C_0 - C_1}{C_0} \times 100\% = \frac{A_0 - A_1}{A_0} \times 100\% \quad (1)$$

Where D is capture capacity, $C_0$, $A_0$, and $C_1$, $A_1$ are the concentrations and absorbance of $Cr_2O_7^{2-}$ solution at 358 nm before and after anion extraction, respectively.

In order to determine the maximum capacity of SD to $Cr_2O_7^{2-}$ and to examine the associated kinetics, the sorption isotherm experiments of SD towards $Cr_2O_7^{2-}$ were determined by varying the initial concentration of $Cr_2O_7^{2-}$ ranging from 10 to 500 mg/L. In a typical experiment, 10 mg of SD was added into 10 mL of an aqueous solution containing a certain concentration of $Cr_2O_7^{2-}$. The resulting mixture was stirred for 2 h to ensure reaching the equilibrium then separated using a 0.22-μm nylon membrane filter. The concentrations of $Cr_2O_7^{2-}$ in solutions were determined by UV-vis spectroscopy on the basis of the typical absorption of $Cr_2O_7^{2-}$ at 358 nm. The amount adsorbed q in mg of $Cr_2O_7^{2-}$ per gram of SD was determined using eq 2:

$$q = \frac{(C_i - C_f)V}{m} \quad (2)$$

where $C_i$=initial concentration (mg/L), $C_f$=final concentration (mg/L), V=volume of solution exposed to SD (L), and m=mass of SD (g). Adsorption isotherms were constructed by monitoring q as a function of time (FIG. 2).

By varying the molar ratios of SD 1•6$PF_6$ to $Cr_2O_7^{2-}$/$ReO_4^-$ and fitting the Langmuir equation, the maximum adsorption capacities can be determined.

Langmuir Equation and Parameters $$\frac{C_e}{q_e} = \left(\frac{1}{Q}\right)C_e + \frac{1}{K_L Q}$$

where $C_e$ is the equilibrium concentration (mg/L), $q_e$ is the equilibrium uptake (mg/g), Q is maximum uptake capacity (mg/g), and $K_L$ is the Langmuir constant (L/mg).

Table 10. Anion Exchange and Capture Kinetics with Various Molar Ratios.

TABLE 10

Anion exchange and capture kinetics with various molar ratios.

| Equivalent of SD | 0.17 | 1 | 1.5 | 2 | 3 | 5 |
|---|---|---|---|---|---|---|
| Ratios of $PF_6^-$ to $Cr_2O_7^{2-}$ | 1:1 | 6:1 | 9:1 | 12:1 | 18:1 | 30:1 |
| Percent Capture (100%) | 29 | 90 | 93 | 96 | 98 | 99 |
| Equilibrium Time (min) | >60 | 60 | 60 | 30 | 15 | 2 |

To balance the removal efficiencies and equivalents of SD, 5 equivalents of SD were used to remove 99% of the anions in 2 min.

$ReO_4^-$ Anion

In a typical experiment, 15 mg of as-synthesized SD 1•6$PF_6$ with the size of 3 μm was immersed in a 10 mL EtOH solution of $Bu_4NReO_4$ (molar ratios of SD 1•6$PF_6$ to $ReO_4^-$ ranging from 0.17:1, 1:1, 2:1, 3:1, 4:1, and 5:1, respectively), and the resulting mixture was shaken gently at room temperature for 30 s. Eight 1.5-mL aliquots of the solution were transferred into 2-mL polypropylene centrifuge tubes at eight time intervals (1, 2, 3, 4, 5, 10, 15 and 20 min) and subjected to centrifugation for 30 s to allow the separation of SD from mixtures. A 0.5-mL aliquot of the supernatant was taken out and injected into a 50-mL metal-free polypropylene centrifuge tube. The remaining solution was collected back into the original vial in order to avoid any loss of the sample. EtOH was removed by flowing $N_2$ gas and the residue was diluted to 10 mL in 3% nitric acid and 3% hydrochloric acid. The concentration of Re and P in each solution was determined by ICP-OES.

TABLE 11

Comparison of $Cr_2O_7^{2-}$ adsorption kinetics and capacities of SD with MOFs.

| Sorbents | Equilibrium time | Capacity (mg g$^{-1}$) | References |
|---|---|---|---|
| SD | 2 min | 357 | This work |
| MOR-2 | 1 min | 194 | J. Mater. Chem. A, 2017, 5, 14707. |
| UiO-66-NH$_2$@silica | 2 h | 277 | J. Mater. Chem. A, 2018, 6, 2742. |
| MOR-1-HA | 5 min | 240 | Chem. Sci. 2016, 7, 2427. |
| ZJU-101 | 10 min | 243 | Chem. Commun. 2015, 51, 14732 |
| [Cu$_2$L(H$_2$O)2(NO$_3$)$_2$•5.5H$_2$O | 160 min | 223 | Chem. Eur. J., 2018, 24, 2718. |
| ABT 2ClO$_4$ | 48 h | 214 | Angew. Chem. Int. Ed. 2013, 52, 13769 |
| BUT-39 | 20 min | 215 | ACS Appl. Mater. Interfaces 2018, 10, 16650. |
| MONT-1 | 24 h | 212 | RSC Adv. 2016, 6, 33888. |
| [Ag(L$^{243}$)](CF$_3$CO$_2$)(H$_2$O) | 320 min | 207 | Chem. Commun. 2017, 53, 9206. |
| 1-SO$_4$ | 24 h | 166 | Angew. Chem., Int. Ed. 2016, 55, 7811. |
| TMU-3 | 10 min | 145 | Inorg. Chem. 2016, 55, 5507. |
| 1-Br | 24 h | 128 | Chem. Commun. 2017, 53, 1860. |
| FIR-54 | 1 h | 103 | Chem. Mater. 2015, 27, 205. |

TABLE 12

Comparison of $ReO_4^-$ adsorption kinetics and capacities of SD with MOFs.

| Sorbents | Equilibrium time (min) | Capacity (mg g$^{-1}$) | References |
|---|---|---|---|
| SD | 2 | 220 | This work |
| NU-1000 | 5 | 210 | Chem. Mater. 2018, 30, 1277. |
| SBN | 10 | 786 | Environ. Sci. Technol. Lett. 2017, 4, 316. |
| SCU-101 | 10 | 217 | J. Am. Chem. Soc. 2017, 139, 14873. |
| SCU-100 | 30 | 541 | Environ. Sci. Technol. 2017, 51, 3471. |
| UiO-66-NH$_3^+$ | >1440 (24 h) | 159 | Inorg. Chem. 2016, 55, 8241. |
| SLUG-21 | 2880 (48 h) | 602 | J. Am. Chem. Soc. 2010, 132, 7202. |

REFERENCES

1 Grimes, J. M., Burroughs, J. N., Gouet, P., Diprose, J. M., Malby, R., Zientara, S., Mertens, P. P. and Stuart, D. I. The atomic structure of the bluetongue virus core. (1998). Nature 395, 470-478.

2 Wikoff, W. R., Liljas, L., Duda, R. L., Tsuruta, H., Hendrix, R. W. and Johnson, J. E. Topologically linked protein rings in the bacteriophage HK97 capsid. (2000). Science 289, 2129-2133.

3 MacGillivray, L. R. and Atwood, J. L. A chiral spherical molecular assembly held together by 60 hydrogen bonds. (1997). Nature 389, 469-472.

4 Heinz, T., Rudkevich, D. M. and Rebek, J., Jr. Pairwise selection of guests in a cylindrical molecular capsule of nanometre dimensions. (1998). Nature 394, 764-766.

5 Olenyuk, B., Whiteford, J. A., Fechtenkotter, A. and Stang, P. J. Self-assembly of nanoscale cuboctahedra by coordination chemistry. (1999). Nature 398, 796-799.

6 Liu, Y. Z., Hu, C. H., Comotti, A. and Ward, M. D. Supramolecular Archimedean cages assembled with 72 hydrogen bonds. (2011). Science 333, 436-440.

7 Pasquale, S., Sattin, S., Escudero-Adan, E. C., Martinez-Belmonte, M. and de Mendoza, J. Giant regular polyhedra from calixarene carboxylates and uranyl. (2012). Nat. Commun. 3, 785-791.

8 Fujita, D., Ueda, Y., Sato, S., Mizuno, N., Kumasaka, T. and Fujita, M. Self-assembly of tetravalent Goldberg polyhedra from 144 small components. (2016). Nature 540, 563-566.

9 Rizzuto, F. J. and Nitschke, J. R. Stereochemical plasticity modulates cooperative binding in a Co(II)$_{12}$L$_6$ cuboctahedron. (2017). Nat. Chem. 9, 903-908.

10 Yang, M., Chan, H., Zhao, G., Bahng, J. H., Zhang, P., Kral, P. and Kotov, N. A. Self-assembly of nanoparticles into biomimetic capsid-like nanoshells. (2017). Nat. Chem. 9, 287-294.

11 Bale, J. B., Gonen, S., Liu, Y., Sheffler, W., Ellis, D., Thomas, C., Cascio, D., Yeates, T. O., Gonen, T. and King, N. P. Accurate design of megadalton-scale two-component icosahedral protein complexes. (2016). Science 353, 389-394.

12 Hsia, Y., Bale, J. B., Gonen, S., Shi, D., Sheffler, W., Fong, K. K., Nattermann, U., Xu, C., Huang, P.-S. and Ravichandran, R. Design of a hyperstable 60-subunit protein icosahedron. (2016). Nature 535, 136-139.

13 Fiedler, D., Leung, D. H., Bergman, R. G. and Raymond, K. N. Selective molecular recognition, C—H bond activation, and catalysis in nanoscale reaction vessels. (2005). Acc. Chem. Res. 38, 349-358.

14 Rebek, J., Jr. Simultaneous encapsulation: molecules held at close range. (2005). Angew. Chem. Int. Ed. 44, 2068-2078.

15 Ma, Y., Nolte, R. J. M. and Cornelissen, J. J. Virus-based nanocarriers for drug delivery. (2012). Adv. Drug Delivery Rev. 64, 811-825.

16 Mal, P., Breiner, B., Rissanen, K. and Nitschke, J. R. White phosphorus is air-stable within a self-assembled tetrahedral capsule. (2009). Science 324, 1697-1699.

17 Pluth, M. D., Bergman, R. G. and Raymond, K. N. Acid catalysis in basic solution: A supramolecular host promotes orthoformate hydrolysis. (2007). Science 316, 85-88.

18 Kaphan, D. M., Levin, M. D., Bergman, R. G., Raymond, K. N. and Toste, F. D. A supramolecular microenvironment strategy for transition metal catalysis. (2015). Science 350, 1235-1238.

19 Yamagishi, H., Sato, H., Hori, A., Sato, Y., Matsuda, R., Kato, K. and Aida, T. Self-assembly of lattices with high structural complexity from a geometrically simple molecule. (2018). Science 361, 1242-1246.

20 Nath, S., Banerjee, R. and Sen, U. A novel 8-nm protein cage formed by *Vibrio cholerae* acylphosphatase. (2014). J. Mol. Biol. 426, 36-38.

21 Field, J. E. The mechanical and strength properties of diamond. (2012). Rep. Prog. Phys. 75, 126505.

22 Zaworotko, M. J. Crystal engineering of diamondoid networks. (1994). Chem. Soc. Rev. 23, 283-288.

23 Schwertfeger, H., Fokin, A. A. and Schreiner, P. R. Diamonds are a chemist's best friend: diamondoid chemistry beyond adamantane. (2008). Angew. Chem. Int. Ed. 47, 1022-1036.

24 Evans, O. R., Xiong, R.-G., Wang, Z., Wong, G. K. and Lin, W. Crystal engineering of acentric diamondoid metal-organic coordination networks. (1999). Angew. Chem. Int. Ed. 38, 536-538.

25 Carrington, E. J., McAnally, C. A., Fletcher, A. J., Thompson, S. P., Warren, M. and Brammer, L. Solvent-switchable continuous-breathing behaviour in a diamondoid metal-organic framework and its influence on $CO_2$ versus $CH_4$ selectivity. (2017). Nat. Chem. 9, 882-889.

26 Beaudoin, D., Maris, T. and Wuest, J. D. Constructing monocrystalline covalent organic networks by polymerization. (2013). Nat. Chem. 5, 830-834.

27 Li, Z., Li, H., Guan, X., Tang, J., Yusran, Y., Li, Z., Xue, M., Fang, Q., Yan, Y., Valtchev, V. et al. Three-dimensional ionic covalent organic frameworks for rapid, reversible, and selective ion exchange. (2017). J. Am. Chem. Soc. 139, 17771-17774.

28 Han, X., Huang, J., Yuan, C., Liu, Y. and Cui, Y. Chiral 3d covalent organic frameworks for high performance liquid chromatographic enantioseparation. (2018). J. Am. Chem. Soc. 140, 892-895.

29 Ma, T. Q., Kapustin, E. A., Yin, S. X., Liang, L., Zhou, Z. Y., Niu, J., Li, L. H., Wang, Y. Y., Su, J., Li, J. et al. Single-crystal x-ray diffraction structures of covalent organic frameworks. (2018). Science 361, 48-52.

30 Ermer, O. Five-fold diamond structure of adamantane-1,3,5,7-tetracarboxylic acid. (1988). J. Am. Chem. Soc. 110, 3747-3754.

31 Simard, M., Su, D. and Wuest, J. D. Use of hydrogen bonds to control molecular aggregation. Self-assembly of three-dimensional networks with large chambers. (1991). J. Am. Chem. Soc. 113, 4696-4698.

32 Lindeman, S. V., Hecht, J. and Kochi, J. K. The charge-transfer motif in crystal engineering. Self-assembly of acentric (diamondoid) networks from halide salts and carbon tetrabromide as electron-donor/acceptor synthons. (2003). J. Am. Chem. Soc. 125, 11597-11606.

33 He, Y., Xiang, S. and Chen, B. A microporous hydrogen-bonded organic framework for highly selective $C_2H_2/C_2H_4$ separation at ambient temperature. (2011). J. Am. Chem. Soc. 133, 14570-14573.

34 Jones, J. T., Hasell, T., Wu, X., Bacsa, J., Jelfs, K. E., Schmidtmann, M., Chong, S. Y., Adams, D. J., Trewin, A., Schiffman, F. et al. Modular and predictable assembly of porous organic molecular crystals. (2011). Nature 474, 367-371.

35 Tian, J., Zhou, T. Y., Zhang, S. C., Aloni, S., Altoe, M. V., Xie, S. H., Wang, H., Zhang, D. W., Zhao, X., Liu, Y. et al. Three-dimensional periodic supramolecular organic framework ion sponge in water and microcrystals. (2014). Nat. Commun. 5, 5574-5584.

36 Cao, L., Wang, P., Miao, X., Dong, Y., Wang, H., Duan, H., Yu, Y., Li, X. and Stang, P. J. Diamondoid supramolecular coordination frameworks from discrete adamantanoid platinum(II) cages. (2018). J. Am. Chem. Soc. 140, 7005-7011.

37 MacNicol, D. D., Hardy, A. D. and Wilson, D. R. Crystal and molecular structure of a 'hexa-host' inclusion compound. (1977). Nature 266, 611-612.

38 Dubbeldam, D., Calero, S., Ellis, D. E. and Snurr, R. Q. RASPA: molecular simulation software for adsorption and diffusion in flexible nanoporous materials. (2016). Mol. Simul. 42, 81-101.

39 Mastalerz, M. and Oppel, I. M. Rational construction of an extrinsic porous molecular crystal with an extraordinary high specific surface area. (2012). Angew. Chem. Int. Ed. 51, 5252-5255.

40 Avci, C., Imaz, I., Came-Sanchez, A., Pariente, J. A., Tasios, N., Perez-Carvajal, J., Alonso, M. I., Blanco, A., Dijkstra, M., Lopez, C. et al. Self-assembly of polyhedral metal-organic framework particles into three-dimensional ordered superstructures. (2018). Nat. Chem. 10, 78-84.

41 Lin, R. B., He, Y., Li, P., Wang, H., Zhou, W. and Chen, B. Multifunctional porous hydrogen-bonded organic framework materials. (2019). Chem. Soc. Rev. 48, 1362-1389.

42 Zhu, L., Sheng, D., Xu, C., Dai, X., Silver, M. A., Li, J., Li, P., Wang, Y., Wang, Y., Chen, L. et al. Identifying the recognition site for selective trapping of $^{99}TcO_4^-$ in a hydrolytically stable and radiation resistant cationic metal-organic framework. (2017). J. Am. Chem. Soc. 139, 14873-14876.

43 Rapti, S., Sarma, D., Diamantis, S. A., Skliri, E., Armatas, G. S., Tsipis, A. C., Hassan, Y. S., Alkordi, M., Malliakas, C. D., Kanatzidis, M. G. et al. All in one porous material: exceptional sorption and selective sensing of hexavalent chromium by using a $Zr^{4+}$ MOF. (2017). J. Mater. Chem. A 5, 14707-14719.

44 Drout, R. J., Otake, K., Howarth, A. J., Islamoglu, T., Zhu, L., Xiao, C., Wang, S. and Farha, O. K. Efficient capture of perrhenate and pertechnetate by a mesoporous Zr metal—organic framework and examination of anion binding motifs. (2018). Chem. Mater. 30, 1277-1284.
45 El-Mehalmey, W. A., Ibrahim, A. H., Abugable, A. A., Hassan, M. H., Haikal, R. R., Karakalos, S. G., Zaki, O. and Alkordi, M. H. Metal—organic framework@silica as a stationary phase sorbent for rapid and cost-effective removal of hexavalent chromium. (2018). J. Mater. Chem. A 6, 2742-2751.
46. Accelrys Materials Studio Release Notes, Release 7.0 (Accelrys Software Inc.: San Diego, 2013).
S1. Y.-C. He et al., Luminescent anionic metal-organic framework with potential nitrobenzene sensing. *Cryst. Growth Des.* 14, 3174-3178 (2014).
S2. O. V. Dolomanov, L. J. Bourhis, R. J. Gildea, J. A. Howard, H. Puschmann, OLEX2: a complete structure solution, refinement and analysis program. *J Appl. Cryst.* 42, 339-341 (2009).
S3. G. Sheldrick, SHELXT-Integrated space-group and crystal-structure determination. *Acta Cryst.* 71, 3-8 (2015).
S4. G. Sheldrick, A short history of SHELX. *Acta Cryst.* 64, 112-122 (2008).
S5. R. Dovesi et al., CRYSTAL17 User's Manual (University of Torino). CRYSTAL17 *User's Manual (University of Torino)*, (2017).
S6. R. Dovesi et al., Quantum-mechanical condensed matter simulations with CRYSTAL. *Wires Comput Mol Sci* 8, e1360 (2018).
S7. A. D. Becke, Density-functional thermochemistry 0.3. the role of exact exchange. *J. Chem. Phys.* 98, 5648-5652 (1993).
S8. P. J. Stephens, F. J. Devlin, C. F. Chabalowski, M. J. Frisch, Ab-Initio calculation of vibrational absorption and circular-dichroism spectra using density-functional force-fields. *J. Phys. Chem.* 98, 11623-11627 (1994).
S9. C. T. Lee, W. T. Yang, R. G. Parr, Development of the colle-salvetti correlation-energy formula into a functional of the electron-density. *Phys. Rev. B* 37, 785-789 (1988).
S10. M. R. Ryder, L. Dona, J. G. Vitillo, B. Civalleri, Understanding and controlling the dielectric response of metal-organic frameworks. *ChemPlusChem* 83, 308-316 (2018).
S11. M. F. Peintinger, D. V. Oliveira, T. Bredow, Consistent Gaussian basis sets of triple-zeta valence with polarization quality for solid-state calculations. *J. Comput. Chem.* 34, 451-459 (2013).
S12. C. G. Broyden, The convergence of a class of double-rank minimization algorithms 1. general considerations. *J. Inst. Maths Applics* 6, 76-90 (1970).
S13. C. G. Broyden, The convergence of a class of double-rank minimization algorithms: 2. the new algorithm. *J. Inst. Maths Applics* 6, 222-231 (1970).
S14. R. Fletcher, A new approach to variable metric algorithms. *Comput. J.* 13, 317-322 (1970).
S15. D. Goldfarb, A family of variable-metric methods derived by variational means. *Math. Comput.* 24, 23-26 (1970).
S16. D. F. Shanno, Conditioning of quasi-newton methods for function minimization. *Math. Comput.* 24, 647-656 (1970).

We claim:

1. A composition comprising an organic ion and a counterion, wherein the organic ion comprises a molecular hub and arms extending therefrom and wherein the organic ion is capable of adopting a tripodal conformation, wherein the organic ion is hexakis[(4,4'-bipyridin-1-ium)methylene]benzene.

2. The composition of claim 1, wherein the organic ion is hexacationic.

3. The composition of claim 1, wherein the counterion is $PF_6^-$ or $AsF_6^-$.

4. The composition of claim 1, wherein the organic ion is hexacationic hexakis[(4,4'-bipyridin-1-ium)methylene]benzene and the counter ion is $PF_6^-$ or $AsF_6^-$.

5. A supramolecular assembly comprising the composition of claim 1, wherein four organic ions form a truncated tetrahedral subunit.

6. The supramolecular assembly of claim 5, wherein the counterion is positioned within a cavity formed by the organic ion in a tripodal confirmation.

7. The supramolecular assembly of claim 5, wherein the organic ion has $D_{3d}$ symmetry.

8. The supramolecular assembly of claim 5, wherein the arms of adjacent organic ions are aligned anti-parallel.

9. The supramolecular assembly of claim 5, wherein ten truncated tetrahedral subunits form a diamondoid unit.

10. The supramolecular assembly of claim 9, the diamondoid unit forms a pore.

11. A crystalline composition comprising composition of claim 1 in the cubic, $Fd\bar{3}$ space group.

12. The crystalline composition of claim 11, wherein the crystalline composition is porous.

13. The crystalline composition of claim 11, wherein crystalline composition has a unit cell comprising 16 organic ions.

14. A method of preparing a supramolecular assembly or a crystalline composition, the method comprising precipitating a solution comprising the composition of claim 1.

15. The method of claim 14, wherein the solution is precipitated by mixing the solution with an anti-solvent or wherein the solution is precipitated by slow vapor diffusion of an anti-solvent.

16. A method for sequestering an ionic contaminant, the method comprising contacting a supramolecular assembly or a crystalline composition with the ionic contaminant, wherein the supramolecular assembly or crystalline composition comprises the composition of claim 1.

17. The method of claim 16, wherein the contacting step exchanges at least a portion of the counterion within the supramolecular assembly or crystalline composition with the ionic contaminant.

18. The method of claim 17, wherein the ionic contaminant is an oxoanion.

19. The method of claim 16 further comprising regenerating the supramolecular assembly or the crystalline composition.

* * * * *